United States Patent
Yu et al.

(10) Patent No.: US 10,390,698 B2
(45) Date of Patent: Aug. 27, 2019

(54) CONDUCTIVE AND STRETCHABLE POLYMER COMPOSITE

(71) Applicants: Hongbin Yu, Chandler, AZ (US); Jignesh Vanjaria, Tempe, AZ (US); Todd Houghton, Tempe, AZ (US)

(72) Inventors: Hongbin Yu, Chandler, AZ (US); Jignesh Vanjaria, Tempe, AZ (US); Todd Houghton, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 101 days.

(21) Appl. No.: 15/625,893

(22) Filed: Jun. 16, 2017

(65) Prior Publication Data
US 2017/0362423 A1    Dec. 21, 2017

Related U.S. Application Data

(60) Provisional application No. 62/351,006, filed on Jun. 16, 2016.

(51) Int. Cl.
*H01B 1/14* (2006.01)
*A61B 5/00* (2006.01)
(Continued)

(52) U.S. Cl.
CPC .................................. *A61B 5/00* (2013.01);
*C08J 3/21* (2013.01); *C08L 65/00* (2013.01);
*H01B 1/14* (2013.01);
(Continued)

(58) Field of Classification Search
CPC ........ A61B 2562/0261; A61B 2562/12; A61B 5/00; C08G 2261/94; C08G 2261/1424;
(Continued)

(56) References Cited

U.S. PATENT DOCUMENTS 4,922,059 A    5/1990   Walker et al.
5,008,496 A    4/1991   Schmidt et al.
(Continued)

FOREIGN PATENT DOCUMENTS

CN    1610168        4/2005
WO    2001094253    12/2001
(Continued)

OTHER PUBLICATIONS

Hu, L.; Cui, H. Energy Environ. Sci. 2012, 6423-6435.
(Continued)

*Primary Examiner* — Mark Kopec
*Assistant Examiner* — Jaison P Thomas
(74) *Attorney, Agent, or Firm* — Michael Best & Friedrich LLP

(57) ABSTRACT

Disclosed herein is a composite prepared by dispersing silver flakes in a polyvinyl alcohol (PVA), phosphoric acid ($H_3PO_4$), and poly(3,4-ethyl-ene-dioxythiophene) (PEDOT):poly(styrene sulfonic acid) (PSS) polymer mixture. The polymer blend can provides conductive pathways between the silver flakes, leading to superior electrical properties even at large deformations.

20 Claims, 17 Drawing Sheets

(51) Int. Cl.
*C08L 65/00* (2006.01)
*C08J 3/21* (2006.01)

(52) U.S. Cl.
CPC ... *A61B 2562/0261* (2013.01); *A61B 2562/12* (2013.01); *C08G 2261/1424* (2013.01); *C08G 2261/3223* (2013.01); *C08G 2261/51* (2013.01); *C08G 2261/62* (2013.01); *C08G 2261/794* (2013.01); *C08G 2261/94* (2013.01); *C08J 2329/04* (2013.01); *C08J 2425/18* (2013.01); *C08J 2465/00* (2013.01); *C08L 2205/03* (2013.01)

(58) Field of Classification Search
CPC ........ C08G 2261/3223; C08G 2261/51; C08G 2261/62; C08G 2261/794; C08L 65/00; C08L 25/18; C08L 29/04; C08L 2205/03; C08K 3/08; C08J 2329/04; C08J 2425/18; C08J 2465/00; C08J 3/21; H01B 1/14
See application file for complete search history.

(56) References Cited

U.S. PATENT DOCUMENTS

| | | |
|---|---|---|
| 5,115,344 A | 5/1992 | Jaskie |
| 5,121,297 A | 6/1992 | Haas |
| 5,168,384 A | 12/1992 | Genba |
| 5,519,596 A | 5/1996 | Woolverton |
| 5,648,771 A | 7/1997 | Halgren et al. |
| 5,903,440 A | 5/1999 | Blazier et al. |
| 5,969,783 A | 10/1999 | Takiar et al. |
| 6,050,962 A | 4/2000 | Kramer et al. |
| 6,299,337 B1 | 10/2001 | Bachl et al. |
| 6,384,890 B1 | 5/2002 | Takiar et al. |
| 6,455,931 B1 | 9/2002 | Hamilton, Jr. et al. |
| 6,476,733 B1 | 11/2002 | Amiri |
| 6,482,540 B1 | 11/2002 | Gozdz et al. |
| 6,584,857 B1 | 7/2003 | Furlani et al. |
| 6,695,457 B2 | 2/2004 | van Drieenhuizen et al. |
| 6,880,955 B2 | 4/2005 | Lin |
| 6,936,855 B1 | 8/2005 | Harrah |
| 7,201,511 B2 | 4/2007 | Moriyama et al. |
| 7,215,547 B2 | 5/2007 | Chang et al. |
| 7,265,719 B1 | 9/2007 | Moosbrugger et al. |
| 7,513,664 B2 | 4/2009 | Chou |
| 8,080,736 B2 | 12/2011 | DeNatale et al. |
| 8,658,904 B2 | 2/2014 | Naganuma et al. |
| 9,706,646 B2 | 7/2017 | Jiang et al. |
| 2002/0094701 A1 | 7/2002 | Biegelsen et al. |
| 2003/0122476 A1 | 7/2003 | Wang et al. |
| 2004/0118595 A1 | 6/2004 | Flammer et al. |
| 2004/0172820 A1 | 9/2004 | Lopez |
| 2005/0099361 A1 | 5/2005 | Majer |
| 2005/0110702 A1 | 5/2005 | Aoki et al. |
| 2005/0280157 A1 | 12/2005 | Roush et al. |
| 2006/0063351 A1 | 3/2006 | Jain |
| 2006/0082298 A1 | 4/2006 | Becken et al. |
| 2006/0113279 A1 | 6/2006 | Little |
| 2007/0090457 A1 | 4/2007 | Lee et al. |
| 2007/0166845 A1 | 7/2007 | Yokokawa |
| 2007/0270315 A1 | 11/2007 | Saruwatari et al. |
| 2008/0093110 A1 | 4/2008 | Bagung |
| 2008/0093118 A1 | 4/2008 | Takahashi et al. |
| 2008/0101070 A1 | 5/2008 | Chou |
| 2008/0125510 A1 | 5/2008 | Crosby et al. |
| 2008/0158498 A1 | 7/2008 | Chang et al. |
| 2008/0179079 A1 | 7/2008 | Ishii et al. |
| 2008/0289859 A1 | 11/2008 | Mikado et al. |
| 2009/0009046 A1 | 1/2009 | Oh et al. |
| 2009/0103295 A1 | 4/2009 | Wang |
| 2009/0167171 A1 | 7/2009 | Jung et al. |
| 2009/0207560 A1 | 8/2009 | Lee |
| 2009/0283891 A1 | 11/2009 | Dekker et al. |
| 2009/0297776 A1 | 12/2009 | Crosby et al. |
| 2009/0310209 A1 | 12/2009 | Aschwanden et al. |
| 2009/0310221 A1 | 12/2009 | Aschwanden |
| 2010/0011529 A1 | 1/2010 | Won et al. |
| 2010/0040846 A1* | 2/2010 | Bahnmuller ........... C09D 11/52 428/208 |
| 2010/0053207 A1 | 3/2010 | Cohen et al. |
| 2010/0143677 A1 | 6/2010 | Lee et al. |
| 2010/0149640 A1 | 6/2010 | Paek et al. |
| 2010/0307705 A1 | 12/2010 | Rahm et al. |
| 2011/0096545 A1 | 4/2011 | Chang |
| 2011/0227822 A1 | 9/2011 | Shai |
| 2011/0228536 A1 | 9/2011 | Im et al. |
| 2012/0119626 A1* | 5/2012 | Takahashi ............... G06F 3/044 310/363 |
| 2012/0138347 A1* | 6/2012 | Bahnmuller ........... C09D 11/52 174/257 |
| 2012/0143525 A1 | 6/2012 | Chen et al. |
| 2012/0146050 A1 | 6/2012 | Adan et al. |
| 2012/0168009 A1 | 7/2012 | Chen et al. |
| 2012/0170244 A1 | 7/2012 | Kwon et al. |
| 2012/0202101 A1 | 8/2012 | Jeda |
| 2012/0212820 A1 | 8/2012 | Jiang et al. |
| 2012/0292504 A1 | 11/2012 | Nojima |
| 2013/0266795 A1* | 10/2013 | Schultz .................... C09D 5/24 428/323 |
| 2014/0204300 A1 | 7/2014 | Park et al. |
| 2014/0287159 A1* | 9/2014 | Carmody ................. C09D 5/24 427/555 |
| 2015/0342050 A1 | 11/2015 | Jiang et al. |
| 2016/0313478 A1 | 10/2016 | Lee et al. |

FOREIGN PATENT DOCUMENTS

| | | | |
|---|---|---|---|
| WO | 03-021679 | 3/2003 | |
| WO | WO-2008031015 A1 * | 3/2008 | ............ C09D 11/52 |
| WO | 2014029908 | 2/2014 | |
| WO | 2014113489 | 7/2014 | |

OTHER PUBLICATIONS

Huang, J.; Zhu, H.; Chen, Y.; Preston, C.; Rohrbach, K.; Cumings, J.; Hu, L. ACS Nano 2013, 2106-2113.
Dragoman, M.; Flahaut, E.; Dragoman, D.; Al Ahmad, M.; Plana, R. Nanotechnology 2009, 375203.
Liu, H.; Crooks, R. M. Anal. Chem. 2012, 2528-2532.
Lankelma, J.; Nie, Z.; Carrilho, E.; Whitesides, G. M. Anal. Chem. 2012, 4147-4152.
Liu, H.; Crooks, R. M. J. Am. Chem. Soc. 2011, 17564-17566.
Dungchai, W.; Chailapakul, O.; Henry, C. S. Anal. Chem. 2009, 5821-5826.
Martinez, A. W.; Phillips, S. T.; Whitesides, G. M.; Carrilho, E. Anal. Chem. 2010, 3-10.
Siegel, A. C.; Phillips, S. T.; Wiley, B. J.; Whitesides, G. M. Lab Chip 2009, 2775-2781.
Hu, L.; Zheng, G.; Yao, J.; Liu, N.; Weil, B.; Eskilsson, M.; Karabulut, E.; Ruan, Z.; Fan, S.; Bloking, J. T.; McGehee, M. D.; Wagberg, L.; Cui, Y. Energy Environ. Sci. 2013, 513-518.
Russo, A.; Ahn, B. Y.; Adams, J. J.; Duoss, E. B.; Bernhard, J. T.; Lewis, J. A. Adv. Mater. 2011, 3426-3430.
Yuan, L.; Yao, B.; Hu, B.; Huo, K.; Chen, W.; Zhou, J. Energy Environ. Sci. 2013, 470-476.
Olsson, H.; Carlsson, D. O.; Nystrom, G.; Sjodin, M.; Nyholm, L.; Stromme, M. J. Mater. Sci. 2012, 5317-5325.
Razaq, A.; Nyholm, L.; Sjödin, M.; Strømme, M.; Mihranyan, A. Adv. Energy Mater. 2012, 445-454.
Jabbour, L.; Destro, M.; Chaussy, D.; Gerbaldi, C.; Penazzi, N.; Bodarno, S.; Beneventi, D. Cellulose 2013, 571-582.
Chun, S. J.; Choi, E. S.; Lee, E. H.; Kim, J. H.; Lee, S. Y.; Lee, S. Y. J. Mater. Chem. 2012, 16618-16626.
Xu, S.; Zhang, Y.; Cho, J.; Lee, J.; Huang, X.; Jia, L.; Fan, J. A.; Su, Y.; Su, J.; Zhang, H.; Cheng, H.; Lu, B.; Yu, C.; Chuang, C.; Kim, T. I.; Song, T.; Shigeta, K.; Kang, S.; Dagdeviren, C.; Petrov, I.; Braun, P. V.; Huang, Y.; Paik, U.; Rogers, R. A. Nat. Commun. 2013, 1543.

(56) References Cited

OTHER PUBLICATIONS

Jost, K.; Perez, C. R.; McDonough, J. K.; Presser, V.; Heon, M.; Dion, G.; Gogotsi, Y. Energy Environ. Sci. 2011, 5060-5067.
Sun, C.; Zhu, H.; Baker, E. B., III; Okada, M.; Wan, J.; Ghemes, A.; Inoue, Y.; Hu, L.; Wang, Y. Nano Energy 2013, DOI: 10.1016/j.nanoen.2013.03.020.
Liu, Y.; Gorgutsa, S.; Santato, C.; Skorobogatiy, M. J. Electrochem. Soc. 2012, A349-A356.
Hu, L.; Choi, J. W.; Yang, Y.; Jeong, S.; La Mantia, F. ; Cui, L. F.; Cui, Y. Proc. Natl. Acad. Sci. U.S.A. 2009, 21490.
Hu, L.; Wu, H.; La Mantia, F.; Yang, Y.; Cui, Y. ACS Nano 2011, 5843-5848.
Gui, Z.; Zhu, H.; Gillette, E.; Han, X.; Rubloff, G. W.; Hu, L.; Lee, S. B. ACS Nano 2013, 6037-6046.
Kang, Y. J.; Chun, S. J.; Lee, S. S.; Kim, B. Y.; Kim, J. H.; Chung, H.; Lee, S. Y.; Kim, W. ACS Nano 2012, 6400-6406.
Kang, Y. R.; Li, Y. L.; Hou, F.; Wen, Y. Y.; Su, D. Nanoscale 2012, 3248-3253.
Weng, Z.; Su, Y.; Wang, D. W.; Li, F.; Du, J.; Cheng, H. M. Adv. Energy Mater. 2011, 917-922.
Zheng, G.; Hu, L.; Wu, H.; Xie, X.; Cui, Y. Energy Environ. Sci. 2011, 3368-3373.
Chen, P.; Chen, H.; Qiu, J.; Zhou, C. Nano Res. 2010, 594-603.
Zhong, Q.; Zhong, J.; Hu, B.; Hu, Q.; Zhou, J.; Wang, Z. L. Energy Environ. Sci. 2013, 1779-1784.
Fan, K.; Peng, T.; Chen, J.; Zhang, X.; Li, R. J. Mater. Chem. 2012, 16121-16126.
Zhang, L.; Zhou, M.; Wen, D.; Bai, L.; Lou, B.; Dong, S. Biosens. Bioelectron. 2012, 155-159.
Xie, X.; Pasta, M.; Hu, L.; Yang, Y.; McDonough, Y.; Cha, J.; Criddle, C. S.; Cui, Y. Energy Environ. Sci. 2011, 1293-1297.
Gardner, J. P.; Mather, J. C.; Clampin, M.; Doyon, R.; Greenhouse, M. A.; Hammel, H. B.; Hutchings, J. B.; Jakobsen, P.; Lilly, S. J.; Long, K. S.; Lunine, J. I.; McCaughrean, M. J.; Mountain, M.; Nella, J.; Rieke, G. H.; Rieke, M. J.; Rix, H. W.; Smith, E. P.; Sonneborn, G.; Stiavelli, M.; Stockman, H. S.; Windhorst, R. A.; Wright, G. S. Space Sci. Rev. 2006, 485-606.
Ahn, B. Y.; Shoji, D.; Hansen, C. J.; Hong, E.; Dunand, D. C.; Lewis, J. A. Adv. Mater. 2010, 2251-2254.
Wei, Z. Y.; Guo, Z. V.; Dudte, L.; Liang, H. Y.; Mandevan, L. Phys. Rev. Lett. 2013, 215501.
Schenk, M.; Guest, S. D. Proc. Natl. Acad. Sci. U.S.A. 2013, 3276.
An, B.; Benbernou, N.; Demaine, E. D.; Rus, D. Robotica 2011, 87-102. Nano Letters Letter 4973 dx.doi.org/10.1021/nl4030374 | Nano Lett. 2013, 13, 4969-4974.
Wang, C.; Nosaka, T.; Yost, B.; Zimmerman, B.; Sutton, E. D.; Kincaid, E.; Keberle, K.; Iqbal, Q. A.; Mendez, R.; Markowitz, S.; Liu, P.; Alford, T. L.; Chan, C. K.; Chan, K. S.; O'Connell, M. J. Mater. Res. Lett. 2013, 13-18.
Hawkes, E.; An, B.; Benbernou, N. M.; Tanaka, H.; Kim, S.; Demaine, E. D.; Rus, D.; Wood, R. J. Proc. Natl. Acad. Sci. U.S.A. 2010, 12441-12445.
Onal, C. D.; Wood, R. J.; Rus, D. IEEE Int. Conf. Rob. Autom. 2011, 4608-4613.
Paik, J. K. IEEE/RSJ Int. Conf. Intell. Robots Syst. 2011, 414-420.
Miura, K. Map fold a la miura style, its physical characteristics and application to the space science. In Research of Pattern Formation; Takaki, R., Ed.; KTK Scientific Publishers: Tokyo, 1994; pp. 77-90.
Nishiyama, Y. Int. J. Pure Appl. Math. 2012, 269-279.
Miura, K. Method of packaging and deployment of large membranes in space; Technical Report for The Institute of Space and Astronautical Science. Report No. 618, Dec. 1985.
Gaynor, J. F.; Senkevich, J. J.; Desu, S. B. J. Mater. Res. 1996, 1842-1850.
John, J.; Li, Y.; Zhang, J.; Loeb, J. A.; Xu, Y. J. Micromech. Microeng. 2011, 105011.
Kim, E.; Tu, H.; Lv, C.; Jiang, H.; Yu, H.; Xu, Y. Appl. Phys. Lett. 2013, 033506.
Katragadda, R. B.; Xu, Y. Sens. Actuators, A 2008, 169-174.
Lunnon, W. F. Math. Comp. 1968, 192-199.
Demaine, E. D.; O'Rourke, J. A survey of folding and unfolding in computational geometry. In Combinatorial and computational geometry; Goodman, J. E., Pach, J., Welzl, E., Eds.; Mathematical Sciences Research Institute Publications: Cambridge University Press: New York, 2005; pp. 167-211.
Balkcom, D. J.; Mason, M. T. Int. J. Robot. Res. 2008, 613-627.
Song, Z. et al. 'Origami Lithium-ion batteries'. Nature Communications. Jan. 28, 2014. vol. 5. Article No. 3140. pp. 1-6.
Long, J. W. et al. 'Three-dimensional battery architectures'. Chemical Reviews. 2004. vol. 104. No. 10. pp. 4463-4492.
Cheng, Q. et al. 'Folding paper-based lithium batteries for higher areal energy densities'. Nano Letters. Sep. 23, 2013. vol. No. 10. pp. 4969-4974.
Chen Y, Au J, Kazlas P, Ritenour A, Gates H, McCreary M. Flexible active-matrix electronic ink display. Nature 423, 136-136 (2003).
Gelinck GH, et al. Flexible active-matrix displays and shift registers based on solution-processed organic transistors. Nat Mater 3, 106-110 (2004).
Kim S, et al. Low-Power Flexible Organic Light-Emitting Diode Display Device. Adv Mater 23, 3511-+ (2011).
Yoon B, Ham DY, Yarimaga O, An H, Lee CW, Kim JM. Inkjet Printing of Conjugated Polymer Precursors on Paper Substrates for Colorimetric Sensing and Flexible Electrothermochromic Display. Adv Mater 23, 5492-+ (2011).
Kim DH, et al. Stretchable and foldable silicon integrated circuits. Science 320, 507-511 (2008).
Ko HC, et al. A hemispherical electronic eye camera based on compressible silicon optoelectronics. Nature 454, 748-753 (2008).
Kim DH, et al. Epidermal Electronics. Science 333, 838-843 (2011).
Pushparaj VL, et al. Flexible energy storage devices based on nanocomposite paper. Proc Natl Acad Sci U S A 104, 13574-13577 (2007).
Scrosati B. Nanomaterials—Paper powers battery breakthrough. Nat Nanotechnol 2, 598-599 (2007).
Gao KZ, et al. Paper-based transparent flexible thin film supercapacitors. Nanoscale 5, 5307-5311 (2013).
Wang JZ, et al. Highly flexible and bendable free-standing thin film polymer for battery application. Mater Lett 63, 2352-2354 (2009).
Hu LB, Wu H, La Mantia F, Yang YA, Cui Y. Thin, Flexible Secondary Li-Ion Paper Batteries. ACS Nano 4, 5843-5848 (2010).
Ihlefeld JF, Clem PG, Doyle BL, Kotula PG, Fenton KR, Apblett CA. Fast Lithium-Ion Conducting Thin-Film Electrolytes Integrated Directly on Flexible Substrates for High-Power Solid-State Batteries. Adv Mater 23, 5663-+ (2011).
Koo M, et al. Bendable Inorganic Thin-Film Battery for Fully Flexible Electronic Systems. Nano Lett 12, 4810-4816 (2012).
Yu CJ, Masarapu C, Rong JP, Wei BQ, Jiang HQ. Stretchable Supercapacitors Based on Buckled Single-Walled Carbon Nanotube Macrofilms. Advanced Materials 21, 4793-+ (2009).
Li X, Gu TL, Wei BQ. Dynamic and Galvanic Stability of Stretchable Supercapacitors. Nano Lett 12, 6366-6371 (2012).
Hu LB, et al. Stretchable, Porous, and Conductive Energy Textiles. Nano Lett 10, 708-714 (2010).
Kuribayashi K, et al. Self-deployable origami stent grafts as a biomedical application of Ni-rich TiNi shape memory alloy foil. Mater Sci Eng A-Struct Mater Prop Microstruct Process 419, 131-137 (2006).
Belcastro S-M, Hull TC. Modeling the folding of paper into three dimensions using affine transformations. Linear Algebra and its Applications 348, 273-282 (2002).
PCT/US2014/072354 International Search Report and Written Opinion of the International Searching Authority dated Apr. 13, 2015 (15 pages).
PCT/US2014/011710 International Search Report and Written Opinion of the International Searching Authority dated May 12, 2014 (7 pages).
PCT/US2015/059006 International Search Report and Written Opinion of the International Searching Authority dated Feb. 17, 2016 (7 pages).
Sant et al., "An in situ heater for a phase-change-material-based actuation system," J. Micromech. Microeng. 2. 085-39 (2010).
Yang et al., "A latchable microvalve using phase change of paraffin wax," Sensors and Actuators A 134, pp. 194-200 (2007).

(56) References Cited

OTHER PUBLICATIONS

Äyräs P. et al., "Diffraction Gratings in Sol-gel Films by Direct Contact Printing Using a UV-mercury Lamp" 162 Opt. Comms. 215-218 (1999).
Fang Y. et al., "Resonant Waveguild Grating Biosensor for Living Cell Sensing" 91 Biophys. J. 1925-940 (2006).
Gudeman CS. et al., "Using the Grating Lite Valve Device as a Multichannel Variable Optical Attenuator (VOA) for the 1.55-↑m Spectral Region" 4653 Proc. SPIE 56-61 (2002).
Albert K. Harris et al., "Silicone Rubber Substrata: A New Wrinkle in the Study of Cell Locomotion" 208 Science 177-179 (1980).
Huang R., "Kinetic Wrinkling of an Elastic Film on a Viscoelastic Substrate" 53 J. Mech. Phys. Solids 63-89 (2005).
Z. Y. Huang et al., "Nonlinear Analyses of Wrinkles in a Film Bonded to a Compliant Substrate" 53 J. Mech. Phys. Solids 2101-118 (2005).
Wilhelm T. S. Huck et al., "Ordering of Spontaneously Formed Buckles on Planar Surfaces" 16 Langmuir 3497-501 (2000).
Hanqing Jiang et al., "Finite Width Effect of Thin-films Buckling on Compliant substrate: Experimental and Theoretical Studies" 56 J. Mech. Phys. Solids 2585-598 (2008).
Cunjiang Yu et al., "Thermoresponsiveness of Integrated Ultra-Thin Silicon with Poly(N-isopropylacrylamide) Hydrogels" 32 Macromol. Rapid Commun. 820 (2011).
Cunjiang Yu et al., "Silicon Thin Films as Anodes for High-Performance Lithium-Ion batteries with Effective Stress Relaxation" 2 Adv. Energy Mater. 68 (2012).
David C. Duffy et al., "Rapid Prototyping of Microfluidic Systems in Poly(dimethylsiloxane)" 70 Anal. Chem. 4974 (1998).
Daniel H. Raguin and G. Michael Morris, "Antireflection Structured Surfaces for the Infrared Spectral Region" 32 Appl. Opt. 1154-167 (1993).
Christopher M. Stafford et al., "A Buckling-based Metrology for Measuring the Elastic Moduli of Polymetric Thin Films" 3 Nat. Mater. 545-550 (2004).
Chee Wei Wong et al., "Analog Tunable Gratings Driven by Thin-film Piezoelectric Microelectromechanical Actuators" 42 Appl. Opt. 621-626 (2003).
A. Azzam Yasseen et al., "Diffraction Grating Scanners Using Polysilicon Micromotors" 5 IEEE J. Sel. Top. Quantum Electron. 75-82 (1999).
M. Ouyang et al., "Conversion of Some Siloxane Polymers to Silicon Oxide by UV/Ozone Photochemical Processes" 12 Chem. Mater. 1591 (2000).
E. Cerda et al., "Thin Films: Wrinkling of an Elastic Sheet Under Tension" 419 Nature 579 (2002).
Christopher Harrison et al., "Sinusoidal Phase Grating Created by a Tunably Buckled Surface" 85 Appl. Phys. Lett. 4016-4018 (2004).
Ned Bowden et al., "Spontaneous Formation of Ordered Structures in Thin Films of Metals Supported on an Elastomeric Polymer" 393 Nature 146-149 (1998).
Takuya Ohzono and Masatsugu Shimomura, "Geometry-dependent Stripe Rearrangement Processes Induced by Strain on Preordered Microwrinkle Patterns" 21 Langmuir 7230-7237 (2005).
Kevin Chen et al., "Facile Large-area Photolithography of Periodic Sub-micron Structures Using a Self-formed Polymer Mask" 100 App. Phys. Lett 233503 (2012).
F.S. Chen et al., "Holographic Storage in Lithium Niobate" 13 Appl. Phys. Lett. 223 (1968).
Kahp Y. Suh et al., "A Simple Soft Lithographic Route to Fabrication of Poly(ethylene glycol) Microstructures for Protein and Cell Patterning" 25 Biomaterials 557 (2004).
Anne Horn et al., "Ordering and Printing Virus Arrays: A straightforward Way to Functionalize Surfaces" 6 Small 2122 (2010).
Jonathan G. C. Veinot et al., "Fabrication and Properties of Organic Light-Emitting "Nanodiode" Arrays" 2 Nano Lett. 333 (2002).
Yoshihiro Koide et al., "Hot Microcontact Printing for Patterning ITO Surfaces. Methodology, Morphology, Microstructure, and OLED Charge Injection Barrier Imaging" 19 Langmuir 86 (2003).
Cunjiang Yu et al., "Tunable Optical Gratings Based on Buckled Nanoscale Thin Films on Transparent Elastomeric Substrates" 96 Appl. Phys. Lett. 041111 (2010).
Zhiyong Fan et al., "Three-dimensional Nanopillar-array Photovoltaics on Low-cost and Flexible Substrates" 8 Nat. Mat. 648 (2009).
C. Vieu et al., "electron Beam Lithography: Resolution Limits and Applications" 164 Appl. Surf. Sci. 111 (2000).
Burn Jeng Lin, "Deep UV Lithography" 12 J. Vac. Sci. Technol. 1317 (1975).
Leon A. Woldering et al., "Periodic Arrays of Deep Nanopores Made in Silicon with Reactive Ion Etching and Deep UV Lithography" 19 Nanotechnology 145304 (2008).
Dong Sik Kim et al., "Laser-Interference Lithography Tailored for Highly Symmetrically Arranged ZnO Nanowire Arrays" 3 Small 76 (2007).
Johannes de Boor et al., "Three-beam Interference Lithography: Upgrading a Lloyd's Interferometer for Single-exposure Hexagonal Patterning" 34 Opt. Lett. 1783 (2009).
Ampere A Tseng et al., "Nanofabrication by Scanning Probe Microscope Lithography: A Review" 23 J. Vac. Sci. Technol. B 877 (2005).
Younan Xia et al., "Unconventional Methods for Fabricating and Patterning Nanostructures" 99 Chem. Rev. 1823 (1999).
L. Jay Guo, "Nanoimprint Lithography: Methods and Material Requirements" 19 Adv. Mater. 495 (2007).
Helmut Schift, "Nanoimprint Lithography: An Old Story in Modern Times? A Review" 26 J. Vac. Sci. Technol. B 458 (2008).
J. Y. Cheng et al., "Fabrication of Nanostructures with Long-range Order Using Block Copolymer Lithography" 81 Appl. Phys. Lett. 3657 (2002).
Tae-Woo Lee et al., "Soft-Contact Optical Lithography Using Transparent Elastomeric Stamps: Application to Nanopatterned Organic Light-Emitting Devices" 15 Adv. Funct. Mater. 1435 (2005).
John A. Rogers et al., "Using an Elastomeric Phase Mask for Sub-100nm Photolithography in the Optical Near Field" 70 Appl. Phys. Lett. 2658 (1997).
Dong Qin et al., "Photolithography with Transparent Reflective Photomasks" 16 J. Vac. Sci. Technol. B 98 (1998).
Zhi-Yuan Li et al., "Optimization of Elastomeric Phase Masks for Near-field Photolithography" 78 Appl. Phys. Lett. 2431 (2001).
John A. Rogers et al., "Generating ~90 Nanometer Features Using Near-field Contact-mode Photolithography with an Elastomeric Phase Mask" 16 J. Vac. Sci. Technol. B 59 (1998).
Daniel J. Shir et al., "Three-Dimensional Nanofabrication with Elastomeric Phase Masks" 111 J. Phys. Chem. B 12945 (2007).
Alexandra Schweikart and Andreas Fery, "Controlled Wrinkling as a Novel Method for the Fabrication of Patterned Surfaces" 165 Microchim. Acta 249 (2009).
Won Mook Choi et al., "Biaxially Stretchable "Wavy" Silicon Nanomembranes" 7 Nano Lett. 1655 (2007).
Kirill Efimenko et al., "Nested Self-similar Wrinkling Patterns in Skins" 4 Nat. Mater. 293 (2005).
Byung-Ho Jo et al., "Three-Dimensional Micro-Channel Fabrication in Polydimethylsiloxane (PDMS) Elastomer" 9 J. Microelectromech. Syst. 76 (2000).
Conghua Lu et al., "A Lithography-free Method for Directed Colloidal Crystal Assembly Based on Wrinkling" 3 Soft Matter 1530 (2007).
Heinz Schmid et al., "Preparation of Metallic Films on Elastomeric Stamps and their Application for Contact Processing and Contact Printing" 13 Adv. Funct. Mater. 145 (2003).
Cheryl S. Selvanayagam et al., "Nonlinear Thermal Stress/Strain Analyses of Copper Filled TSV (Through Silicon Via) and their Flip-Chip Microbumps" 32 III Trans. Adv. Pack. 720 (2009).
James S. Sharp and Richard. A. L. Jones, "Micro-buckling as a Route Towards Surface Patterning" 14 Adv. Mater. 799 (2002).
Pimpon Uttayarat et al., "Topographic Guidance of endothelial Cells on Silicone Sufraces with Micro-to Nanogrooves: Orientation of Actin Filaments and Focal Adhesions" 75 J. Biomed. Mater. Res. A 668 (2005).

(56) References Cited

OTHER PUBLICATIONS

Cunjiang Yu and Hanquing Jiang, "Forming Wrinkled Stiff Films on Polymeric Substrates at Room Temperature for Stretchable Interconnects Applications" 519 Thin Solid Films 818 (2010).
C. Yu et al., "Stretchable Supercapacitors Based on Buckled Single-Walled Carbon Nanotube Macrofilms", Adv. Mater., 21, pp. 4793-4797 (2009).
C. Yu et al., "A stretchable temperature sensor based on elastically buckled thin film devices on elastomeric substrates", Appl. Phys. Lett. 95, 141902 (2009).
H. Jiang et al., Finite deformation mechanics in buckled thin films on compliant supports, PNAS, vol. 104., No. 40, pp. 15607-15612 (2007).
D.-Y. Khang et al., "A Stretchable Form of Single-Crystal Silicon for High-Performance Electronics on Rubber Substrates", Science, vol. 311 pp. 208-212 (2006).
S.P. Lacour et al., "Stretchable Interconnects for Elastic Electronic Surfaces", Proc. IEEE, vol. 93, No. 8, pp. 1459-1467 (2005).
International Search Report and Written Opinion for PCT/US2014/065776, dated Apr. 22, 2015.
T Ma et al., "Micro-strain sensing using wrinkled stiff thin films on soft substrates as tunable optical grating", Optics Express, vol. 21, No. 10, pp. 11994-12001 (2013).
X. Jiang et al., "Controlling Mammalian Cell Spreading and Cytoskeletal Arrangement with Conveniently Fabricated Continuous Wavy Features on Poly(dimethylsiloxane)", Langmuir 18(8), 3273-3280 (2002).
S. Wagner et al., "Electronic skin: architecture and components," Physica E 25(2-3), 326-334 (2004).
S. P. Lacour et al., "Design and performance of thin metal film interconnects for skin-like electronic circuits," IEEE Electron Device Lett. 25(4), 179-181 (2004).
S. P. Lacour et al., "Stretchable gold conductors on elastomeric substrates," Appl. Phys. Lett. 82(15), 2404-2406 (2003).
S. P. Lacour, S. Wagner, R. J. Narayan, T. Li, and Z. Suo, "Stiff subcircuit islands of diamondlike carbon for stretchable electronics," J. Appl. Phys. 100(1), 014913 (2006).
H. Q. Jiang et al., "Mechanics of precisely controlled thin film buckling on elastomeric substrate," Appl. Phys. Lett. 90(13), 133119 (2007).
K.M. Choi et al., "A photocurable poly(dimethylsiloxane) chemistry designed for soft lithographic molding and printing in the nanometer regime," J. Am. Chem. Soc. 125(14), 4060-4061 (2003).
Song et al., "Origami 1 ithiwn-ion batteries," brochure, Nature Communications, Jan. 8, 2014, vol. 5, article No. 3140, pp. 1-6 see pp. 2-3; Methods in p. 6; figure 1.
Xu et al., "Stretchable batteries with self-similar serpentine interconn. ects and integrated wireless recharging systems", Nature Communications, Feb. 26, 2013, vol. 4, article No. 1543, pp. 1-8 see abstract; pp. 2-4; Methods in p. 7; figures 1-3.
PCT/US2015/052205 International Search Report and Written Opinion of the International Searching Authority dated Dec. 23, 2015 (9 pages).
PCT/US2015/068038 International Search Report and Written Opinion of the International Searching Authority dated May 4, 2016 (9 pages).
Asundi et al., "Optical strain sensor using position-sensitive detector and diffraction grating: error analysis," Optical Engineering 39.6 (2000): 1645-1651.

* cited by examiner

CONDUCTIVE AND STRETCHABLE POLYMER COMPOSITE

CROSS-REFERENCE TO RELATED APPLICATIONS

This application claims priority to U.S. Provisional Patent Application No. 62/351,006, filed on Jun. 16, 2016, the entire contents of which are incorporated herein by reference.

BACKGROUND OF THE INVENTION

Monitoring the status of an individual's physical condition with the help of various external sensors is of general interest. Of particular relevance is the measurement of parameters such as heart rate, pulse-shape, brain activity, blood pressure, or blood glucose content. The onus on the designers looking to design such a sensor is that the sensor must provide maximum functionality without hindering the user mobility by any significant degree. This has led to the evolution of the concept of "electronic skin," a stretchable flexible polymer foil which can be attached to skin and which can incorporate all the essential electronics required for a specific purpose, or even multiple purposes. Fundamental to the success of developing such a sensor is the advancement of stretchable (bio)electronics. This involves the development of electronic devices that retain good functionality even under stretching.

To date, several strategies have been attempted to address this issue. One such strategy has been to exploit novel composite materials. This involves the incorporation of conductive filler materials, such as metal nanoparticles, metal nanotubes, graphite, carbon nanotubes (CNTs), and conducting polymers, into a rubbery polymer matrix through blending. Composites designed for stretchable electronics have attracted increasing attention in recent years because they are potentially more mechanically durable and are more promising for large-scale applications. Current state-of-the-art demonstrations have shown that composites with very high conductivities can be prepared ($\geq 10^3$ S/cm) and that the composites maintain such high conductivities even at very large strains ($\geq 100\%$). However, there exists a limit to this strategy, as the incorporation of high concentrations of conductive fillers, such as CNTs, into the polymer matrix to increase conductivity can result in the decrease of the stretchability of the resultant composite. Also, many nanomaterials are too expensive for most practical applications.

SUMMARY OF THE INVENTION

It is highly desirable to develop a facile, cost-effective, and scalable way to fabricate a high-performance stretchable conductive composite material.

In some embodiments, the disclosure provides a composite, wherein the composite comprises: a conductive polymer; a water-soluble polymer; a plasticizer; and metal flakes, wherein the metal flakes have a diameter of about 1 μm to about 45 μm.

In some embodiments, the disclosure provides a composite, wherein the composite comprises poly(3,4-ethylenedioxythiophene):poly(styrene sulfonic acid) (PEDOT:PSS), polyvinyl alcohol (PVA), phosphoric acid ($H_3PO_4$), and micron-sized silver flakes.

In some embodiments, the disclosure provides a method of preparing a composite, comprising: dissolving the water-soluble polymer in water to form a first solution; adding the plasticizer to the first solution to form a second solution; adding a solution or suspension of the conductive polymer to the second solution to form a polymer blend; and adding the metal flakes to the polymer blend to form the composite.

Other embodiments of the disclosure will become apparent in view of the following description.

DETAILED DESCRIPTION

Figures 1A, 1B:
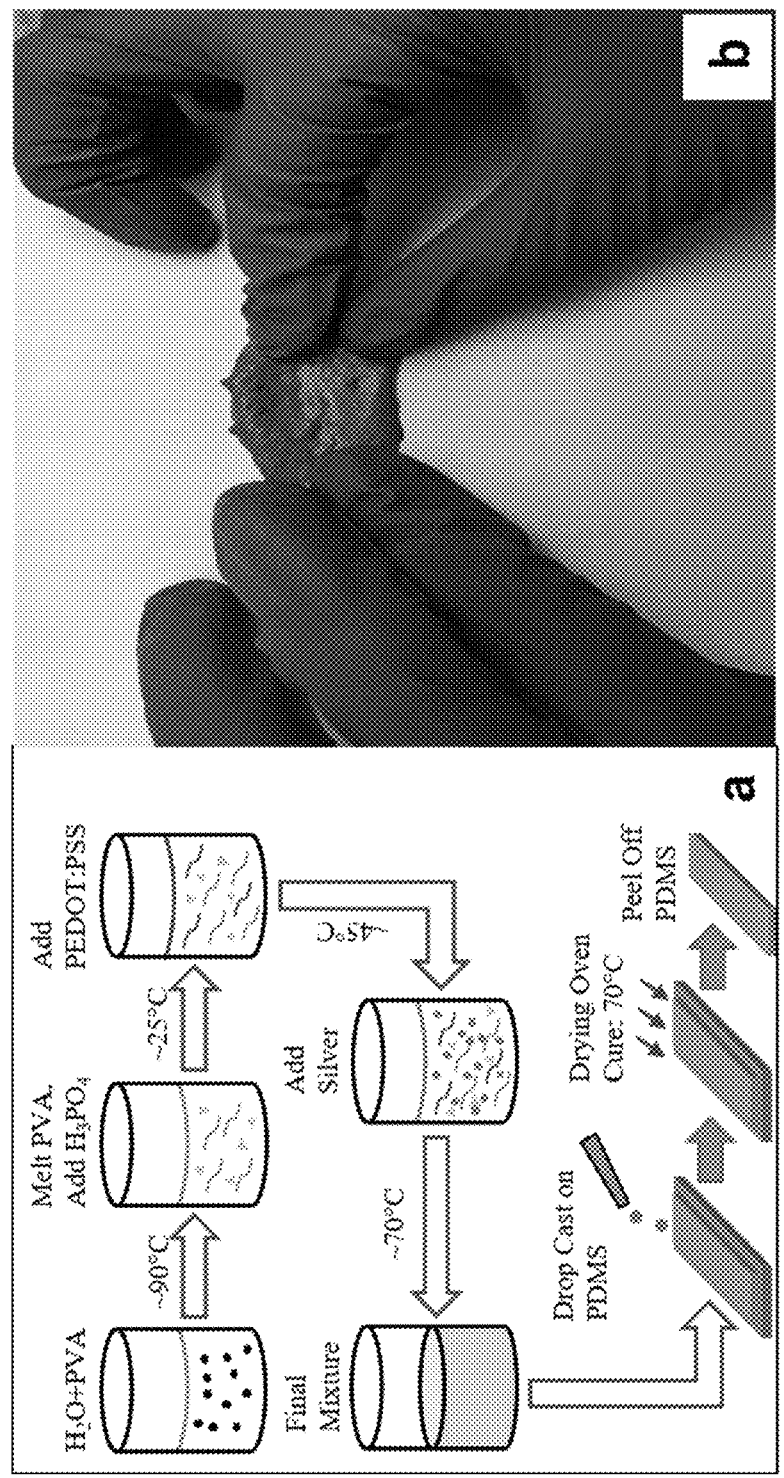
FIG. 1A illustrates a schematic diagram of the synthesis process for the composite films.
FIG. 1B is a photograph of a synthesized composite film after being cured in the drying oven and peeled off the PDMS substrate.

Stretchable and flexible electronic devices have gained significant attention in recent years, as they can be integrated into many systems, such as medical sensors, wearable sensors, displays, and robots. Additionally, they have numerous applications in the consumer, medical, Internet of Things (IoT), and electronic gaming technology spaces due to their unique mechanical properties. One of the primary areas of current research is designing stretchable electronic materials that provide adequate conductivity and mechanical robustness. Metal-based materials have been reported to have the highest conductivity, but are not stretchable enough, while elastomer materials are not conductive enough.

This disclosure provides a highly conductive, stretchable composite. The composite includes a conductive polymer, a water-soluble polymer, a plasticizer, and metal flakes. An exemplary composite includes PVA, phosphoric acid, PEDOT:PSS, and silver flakes. The composites may provide excellent conductivity, stretchability, and flexibility for use as a stretchable electronic material, such as an interconnect, for example. In particular, silver has the highest conductivity of all metals, and is less expensive than other options. The blend of PVA, phosphoric acid, and PEDOT:PSS provides a practical balance between conductivity and stretchability. An exemplary composite may provide conductive pathways between the silver flakes, leading to superior electrical properties even at large deformations (e.g., $R=125\Omega$ at no strain and $R=300\Omega$ at 150% strain). It may also allow for excellent ductility ($\geq 200\%$) even at a high silver loading used during synthesis.

This disclosure also provides capacitive strain gauges based on highly conductive, stretchable composites. Capacitive-type sensors have numerous advantages. They are physically robust, can be constructed from a variety of materials in different shapes and sizes, and have the potential to be manufactured at low cost. Capacitive strain gauges, in particular, are useful for providing a simple platform for testing the electrical and mechanical properties of stretchable materials. A strain gauge is a device used to measure strain on an object.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrase "at least one of A, B, . . . and N" or "at least one of A, B, . . . N, or combinations thereof" are defined in the broadest sense to mean one or more elements selected from the group comprising A, B, . . . and N, that is to say, any combination of one or more elements A, B, . . . or N including any one element alone or in combination with one or more of the other elements, which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4". The term "about" may refer to plus or minus 10% of the indicated number. For example, "about 10%" may indicate a range of 9% to 11%, and "about 1%" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

2. COMPOSITES

The composites of this disclosure include a blend of polymers with micron-sized metal particle flakes. The composites generally include a first polymer that is a conductive polymer, a second polymer that is a water-soluble polymer, a plasticizer, and metal particle flakes.

a. Conductive Polymers

The composite films include a conductive polymer. Exemplary conductive polymers include poly(3,4-ethylenedioxythiophene)-poly(styrenesulfonate) (PEDOT:PSS), polyacetylene (PAC), and polyphenylene vinylene (PPV). In some embodiments, the conductive polymer is a water-soluble or water-dispersible conductive polymer. In some embodiments, the conductive polymer is PEDOT:PSS.

PEDOT:PSS (CAS Number: 155090-83-8) is a polymer mixture of poly(3,4-ethylenedioxythiophene) with polystyrene sulfonate anions. PEDOT:PSS is available from a number of commercial suppliers, including Sigma-Aldrich®. The ratio of PSS to PEDOT may be about 1.0 to about 5.0, e.g., about 2.5. The material is generally available as a dispersion in water at varying weight percentages of dissolved/suspended solids. For the purposes of this disclosure, PEDOT:PSS at a solids content of 0.8% to 2.8% by weight may be suitable, e.g., a solids content of 1.0% by weight.

b. Water-Soluble Polymers

The composite films also include a water-soluble polymer. Exemplary water-soluble polymers include polyvinyl alcohol (PVA), polyethylene glycol (PEG, also known as polyethyleneoxide (PEO) or polyoxyethylene (POE)), and polyvinylpyrrolidone (PVP). Suitable water-soluble polymers will have high stretchability.

The water-soluble polymer may have a molecular weight ranging from about 20 kDa to about 200 kDa, about 125 kDa to about 200 kDa, about 145 kDa to about 200 kDa, or about 145 to about 190 kDa. For preparation of a composite film, the water-soluble polymer may be dissolved in water at a weight percentage range of about 1% to about 15%, or about 2% to about 10%, or about 3% to about 7%.

In some embodiments, the water-soluble polymer is PVA. The PVA may have a molecular weight of about 125 kDa to about 200 kDa, about 145 kDa to about 200 kDa, or about 145 to about 190 kDa. The composite film may be prepared from a solution of PVA in water at a weight percentage range of about 2% to about 10%, or about 3% to about 7%.

c. Plasticizer

The composite films also include a plasticizer. The plasticizer can improve the mechanical and electrical performance of the polymer matrix, for example by allowing the polymers to flex and stretch at significantly reduced forces.

An exemplary plasticizer is phosphoric acid ($H_3PO_4$), which may act as a plasticizer for a water-soluble polymer such as PVA. Phosphoric acid may be used to prepare composite films by incorporating it into an aqueous solution at a weight percentage of about 1% to about 15%, or about 3% to about 9%.

d. Metal Flakes

The composite films also include metal flakes. The metal flakes that are used in the composite films may have diameters in the range of about 1 μm to about 50 μm, e.g., about 1 μm to about 45 μm. Suitably, the metal flakes have an average diameter of about 10 μm. The flake size range may allow many adjacent flakes to overlap with each other in the composite, while the length/width ratio may be small enough to ensure that the flakes can be mixed into the bulk of the polymer matrix without degradation.

Suitable metal flakes include silver, copper, gold, platinum, and zinc metal flakes. In suitable embodiments, the metal flakes are silver flakes.

e. Preparation of Composite Films

Composite films may be synthesized as a viscous solution mixture, using water as a solvent. The water may be deionized water, and may be included in an amount of about 15 wt % to about 75 wt %, or about 25 wt % to about 60 wt %. The mixture of the polymers, plasticizer, and metal flakes in water may be drop casted and dried in a curing oven. Other methods of preparing composite films will be familiar to those skilled in the art.

3. COMPOSITE PROPERTIES

Exemplary composites may exhibit a high degree of stretchability, withstanding strains of about 230% before fracture. Electrical performance of the film can be evaluated with respect to mechanical strain. Unstretched, exemplary composite films may exhibit a sheet resistance of about 85 Ω/sq. When voltage is applied longitudinally, resistance of the film may vary from about 100Ω at 0% strain to about 350Ω at 166% strain.

4. USES OF THE COMPOSITES

Composites described herein can be used to prepare composite films, and may also be used as a stretchable electronic material (e.g., an interconnect) in systems such as medical sensors, displays, robots, wearable sensors, electronic gaming, and strain gauges.

The present disclosure has multiple aspects, illustrated by the following non-limiting examples.

5. EXAMPLES

The foregoing may be better understood by reference to the following examples, which are presented for purposes of illustration and are not intended to limit the scope of the disclosure.

Unless otherwise noted, all of the chemicals required to synthesize the composite, including the silver micron-sized flakes (10 μm, ≥99% trace metal basis), PEDOT:PSS aqueous solution (solid content 1.0% by weight), PVA pellets (MW=140K-189K, 99.9% hydrolyzed), and phosphoric acid ($H_3PO_4$) pellets (crystalline, ≥99% trace metal basis) were obtained from Sigma Aldrich. Poly dimethylsiloxane (PDMS) in the form of Slygard 184 (consisting of pre-polymer and curing agent) was also obtained from Sigma Aldrich.

Optical microscopy was performed using a Nikon Eclipse LV100 apparatus. Electron microscope images were recorded using a Hitachi S-4700-II scanning electron microscope. The chemical compositions of the films, after being subjected to the various stresses and strains as further described below, were determined by energy dispersive x-ray spectroscopy (EDX) using TEAM™ EDS Analysis System coupled to the Hitachi S-4700-II scanning electron microscope.

Example 1

Composite Preparation

To prepare the composite solution, PVA was dissolved in de-ionized water to obtain an about 10 wt % aqueous solution. The solution was heated at about 90° C. until the pellets completely melted. Then, $H_3PO_4$ was added into the hot solution such that the ratio of PVA to $H_3PO_4$ was about 1:1 by weight. The solution was stirred at room temperature (about 23° C.) overnight. Then, a PEDOT:PSS aqueous solution was added to the mixture such that the weight percent of the PEDOT:PSS solution in the resulting solution mixture was about 40%. This resultant polymer blend was then stirred overnight (about 12 hours) at about 45° C. After that, silver flakes were added to the blend such that the weight fraction of silver to PVA was about 1:1. The solution was then further stirred at about 70° C. for ≥12 hours to obtain the composite solution.

To prepare the PDMS substrate, the pre-polymer and curing agent were mixed in a ratio of about 10:1 and were then cured at about 85° C. for about 2 hours. The prepared composite solution was drop casted on the PDMS substrate and cured in a drying oven at about 70° C. until the solution completely solidified. The composite films were then peeled off from the PDMS substrate.

In another embodiment, the PDMS substrate was prepared by pouring the composite solution into petri dishes with a PDMS bottom lining and curing in a drying oven at about 70° C. until the remaining water evaporated. Dried composite thick films were peeled from the PDMS backing. The thick film may optionally be cut into rectangular shapes.

The above process is represented by a schematic diagram, shown in FIG. 1A. The resulting film, after curing and peeling off the PDMS backer is shown in FIG. 1B.

Example 2

Measurement of Film Thickness

The unstretched composite film was gently sandwiched between two copper plates to ensure edge flatness. The composite sample was then placed in front of a laser microscope setup, illuminated, and aligned to the working distance of a 50× objective lens. A low power (about 0.02 mW) laser beam was directed parallel to the objective's optical axis towards the sample surface, generating a small (about 15 μm), highly visible, beam spot on the composite film's cross-section. The spot's location on the composite film cross-section was determined using a beamsplitter cube and CCD camera. Using the video feed from the camera, the laser spot was moved from the bottom of the cross-section to the top using a linear optical stage. The distance traveled by the laser from the bottom of sample to the top was recorded as the film thickness.

Example 3

Mechanical and Electrical Properties Prior to Fatigue Testing

The prepared film was subjected to a tension test using a Ta.XT plus Texture Analyzer. The film was stretched until fracture occurred. The tensile stress applied on the film and the corresponding strain in the film were continuously monitored and recorded.

The sheet resistance of the composite films was measured by the van der Pauw four-point probe technique using an Alessi four point probe machine linked up with a Keithley 2700 source/meter. The resistance was measured at various points to verify uniform resistance throughout the film. The obtained sheet resistance was then multiplied by the thickness of the film to obtain the film resistivity.

Figures 2A, 2B:
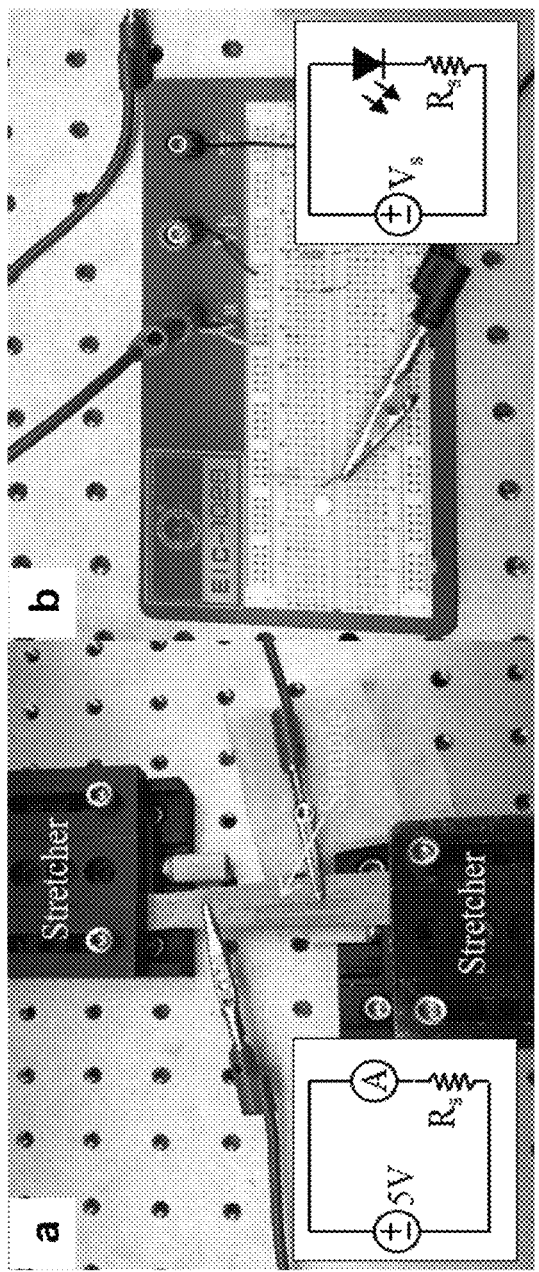
FIG. 2A shows an electrical setup used to measure the resistance of the composite film for various percent strain with the representative circuit diagram (inset).
FIG. 2B is an electrical setup used to measure the turn-on voltage of a red GaAs LED for various percent strain of the composite film, with the representative circuit diagram (inset).

The electrical resistance of the film as a function of the elongation of the composite film could not be measured directly. Hence, it was measured indirectly using a circuit comprising a voltage source, a current meter, and the composite film. The film was affixed between optical clamps and stretched while a constant voltage of about 5V was applied across the film using the voltage source. As the film was stretched, the current in the circuit was recorded. The resistance of the composite film was then calculated by using Ohm's law. The circuit set up to measure the film resistance is shown in FIG. 2A.

The electrical conductance of the film with varying strains was also tested by stretching the film to various percent elongation and measuring the voltage required to light a red GaAs LED with a threshold voltage of about 1.5V. In this setup, the film served as the LED's series resistor, regulating the current of the circuit. The circuit set up to measure the turn voltage of the LED for various film strains is shown in FIG. 2B.

Example 4

Mechanical Fatigue Testing

One of the key parameters of any wearable electronic material is the ability to retain its electrical properties when subjected to repeated stretching. In order to obtain a relationship between stretching cycles and electrical conductivity, two polymer composite samples were subjected to extended tensile fatigue testing using a Ta.XT Texture Analyzer operating in strain cycle mode. The first sample was subjected to 400 strain cycles, with a maximum elongation of about 150% per cycle. The second sample was also strain cycled 400 times, with a maximum elongation of about 100% per cycle. Properties of the films after such testing are shown in FIGS. 4A-C and 5A-C, with further details provided in subsequent Examples.

Example 5

Electrical Properties After Fatigue Cycling

Upon completion of mechanical fatigue cycling as described in Example 4, the first composite film, which was subjected to 400 stretch cycles at an elongation of about 150%, was again affixed between two optical clamps and stretched while a constant value of about 5V was applied across the film strip. As before, the film was stretched while the current though the film was recorded with a digital multimeter. Resistance of the film was calculated and compared to resistances obtained before fatigue cycling. As a final conductivity test, the fatigued film was used as a series resistor for an LED, driven by a 1.5V power supply.

The electrical resistance of the second composite film, which was subjected to 400 strain cycles at about 100% elongation, was determined in situ during the fatigue cycling process. Copper foil was sandwiched against the conductive surface of the PVA film at both the upper and lower sample mount points of a Ta.XT Texture Analyzer, allowing current to flow though the film. Exposed copper foil was then connected using clips to a digital multimeter set in resistance detection mode. The Ta.XT sample mounting pads were covered in scotch tape to prevent electrical contact with the instrument chassis. The resistance of the film was measured at 50 cycle intervals and was recorded when the film had relaxed to about 0% strain. As a final conductivity test, the fatigued film was used as a series resistor for an LED, driven by a 1.5V power supply.

Example 6

Results and Discussion

Microstructure and Chemical Composition of Composite Films Prior to Fatigue Testing.

Figures 3A, 3B:
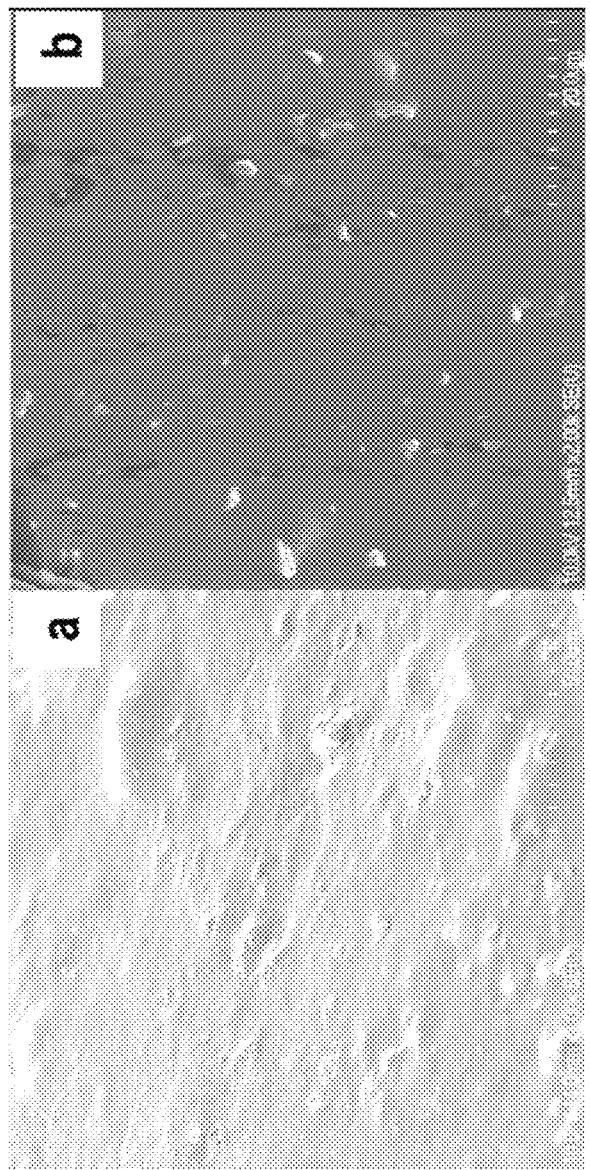
FIG. 3A shows an SEM image of the top section of the film after being subjected to fracture.
FIG. 3B shows an SEM image of the cross section of the film after being subjected to fracture.
Figure 3C:
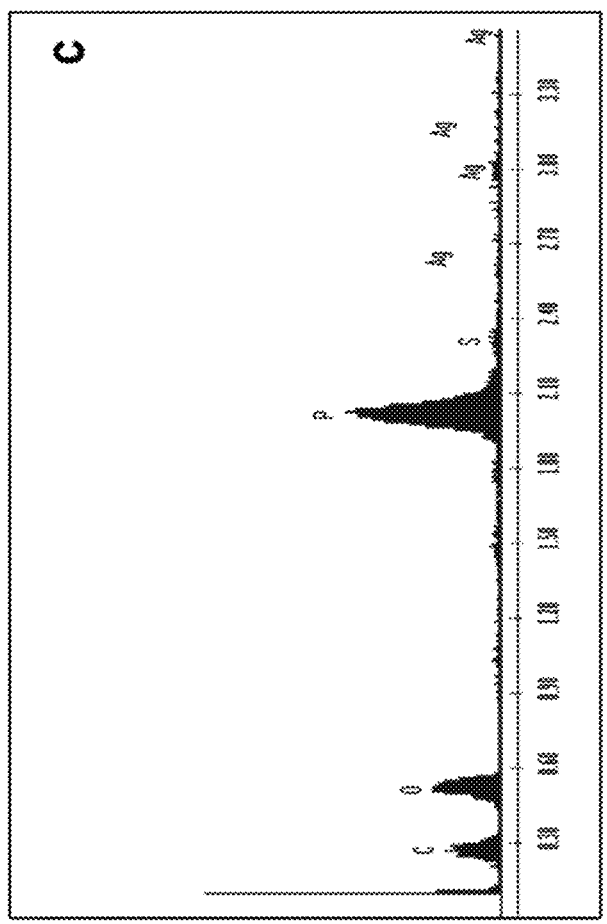
FIG. 3C shows an EDX spectrum of the cross section of the film after being subjected to fracture.

FIGS. 3A and 3B show the scanning electron microscopy (SEM) images of the top section and cross section of the composite films, respectively, after the films were subjected to fracture but prior to fatigue testing. It can be seen from the images that both the top section and cross section are fairly uniform. FIG. 3C shows the EDX spectrum of the cross section of the film. It can be seen there is a high content of carbon, oxygen, and phosphorous in the film. The atomic percent of carbon, oxygen, and phosphorous is 27.6%, 14.8%, and 47.2%, respectively. The carbon can be attributed to the polymers, PEDOT:PSS and PVA, and the phosphorous can be attributed to the phosphoric acid used to synthesize the films. There is also a significant content of silver in the film (7.4 atomic %). This implies that the silver was efficiently incorporated in the polymer backbone during the blending phase. Some white patches can be seen distributed randomly through the film. This is most likely due to super saturation of silver in those spots, leading it to form a separate phase during curing.

Microstructure and Chemical Composition of Composite Films Post Fatigue Testing.

Figures 4A, 4B:
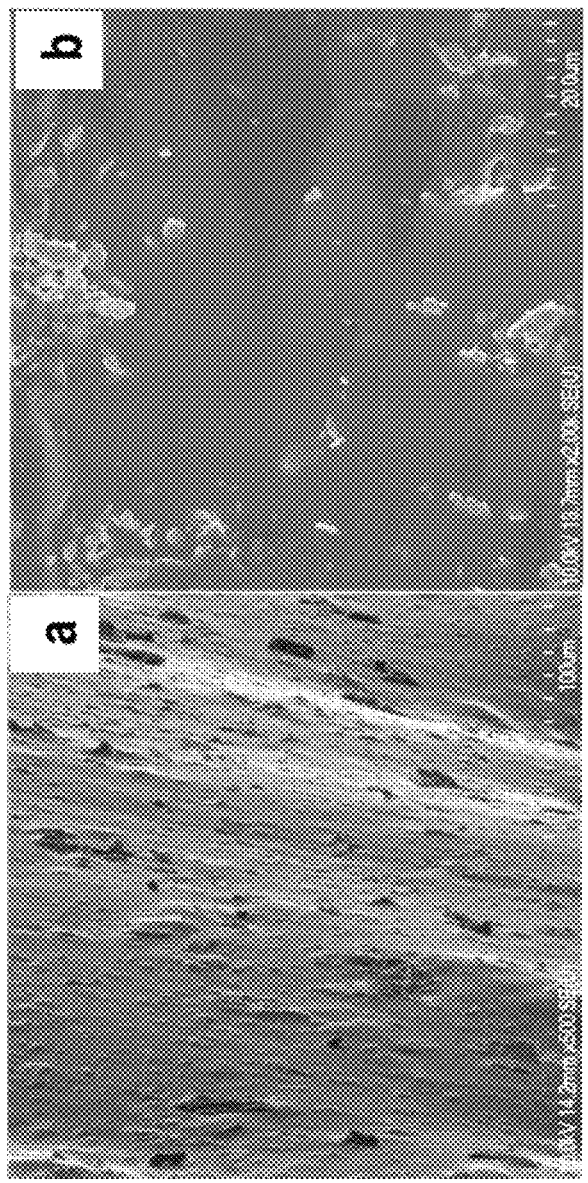
FIG. 4A shows an SEM image of the top section of the film after being subjected to 400 tension cycles at about 100% strain.
FIG. 4B shows an SEM image of the cross section of the film after being subjected to 400 tension cycles at about 100% strain.
Figure 4C:
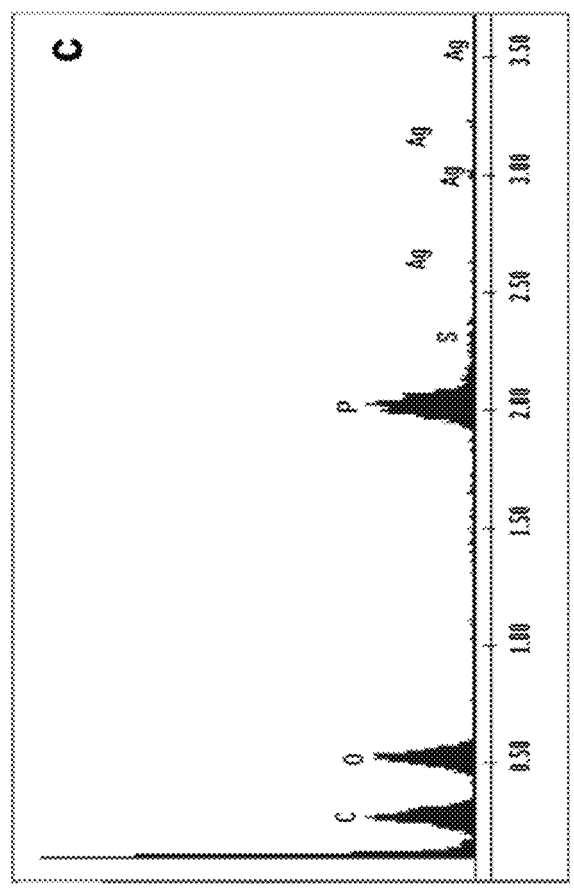
FIG. 4C shows an EDX spectrum of the cross section of the film after being subjected to 400 tension cycles at about 100% strain.

FIGS. 4A and 4B show the SEM images of the top section and cross section of the composite film, respectively, after the film was stretched to 100% and released continuously for 400 cycles. FIG. 4C shows the EDX spectrum of the cross section of the film. It can be seen from the SEM images that there is a higher concentration of silver patches within the cross section. It can also be seen that carbon, oxygen, and phosphorous in the dominant phase has remained similar to that seen in the fractured film, but the silver content has decreased (4.1 atomic %). From this, it can be surmised that the silver particles have broken off from the polymer backbone and have agglomerated into the second phase due to the applied fatigue stress on the film. Such behavior has also been reported previously (Park et al. *Nature Nanotechnology*, vol. 7, no. 12, pp. 803-9, 2012).

Figures 5A, 5B:
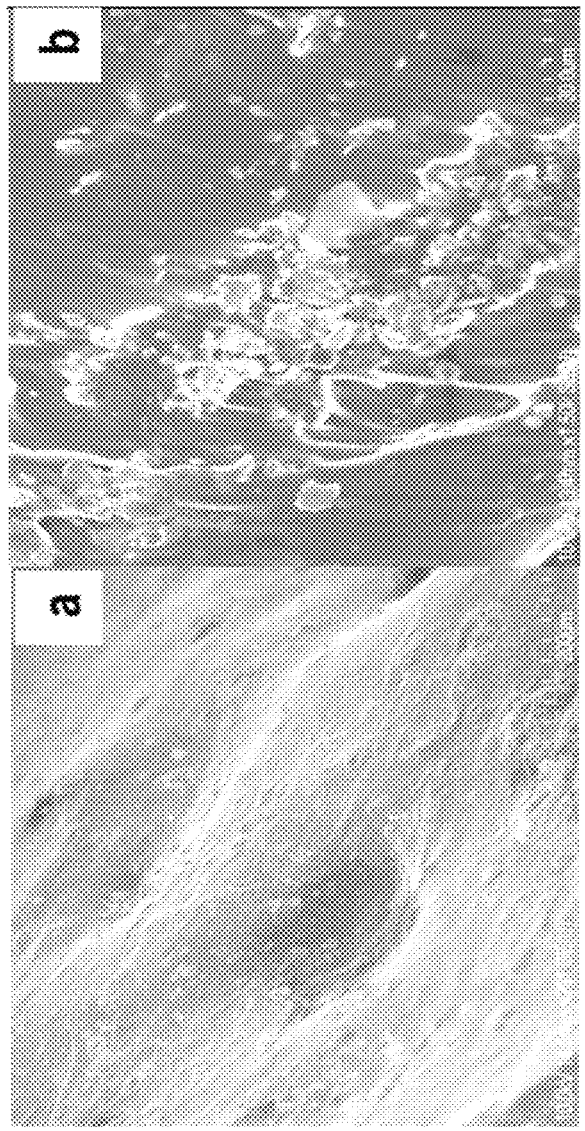
FIG. 5A shows an SEM image of the top section of the film after being subjected to 400 tension cycles at about 150% strain.
FIG. 5B shows an SEM image of the cross section of the film after being subjected to 400 tension cycles at about 150% strain.
Figure 5C:
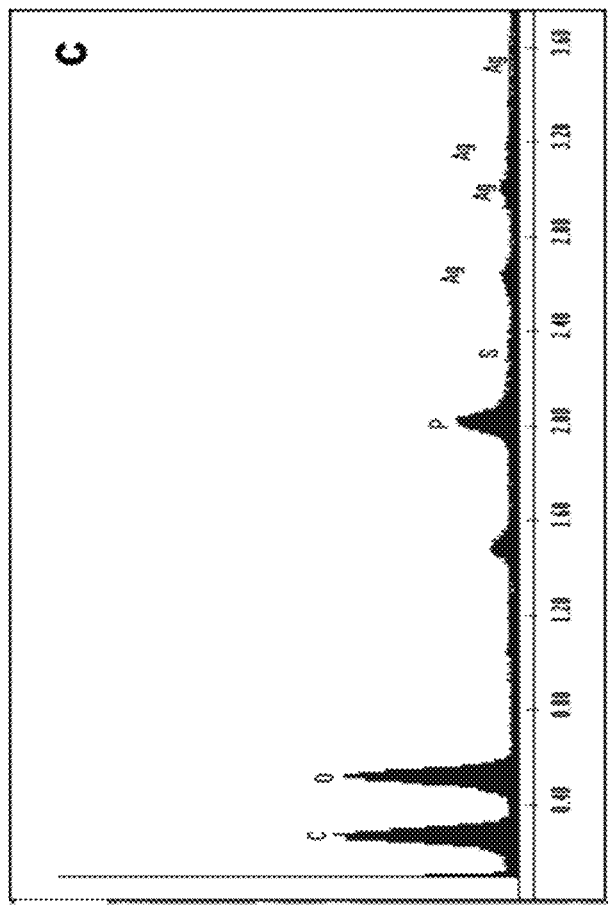
FIG. 5C shows an EDX spectrum of the cross section of the film after being subjected to 400 tension cycles at about 150% strain.

FIGS. 5A and 5B show SEM images of the top section and cross section of the composite film, respectively, after the film was stretched to 150% and released continuously for 400 cycles. FIG. 5C shows the EDX analysis of the cross section of the film. It can be seen from the SEM images that there is an even higher density of silver patches within the cross section, as compared to film subjected to fatigue testing at 100% strain. It can also be seen that the silver content in the dominant phase of the film has further decreased (1.4 atomic %). Thus, it can be inferred that the higher fatigue stress applied on the film led to a greater extent of the silver breaking away from the dominant phase and combining in a separate phase.

Mechanical and Electrical Properties of Composite Films Prior to Fatigue Testing.

Figure 6:
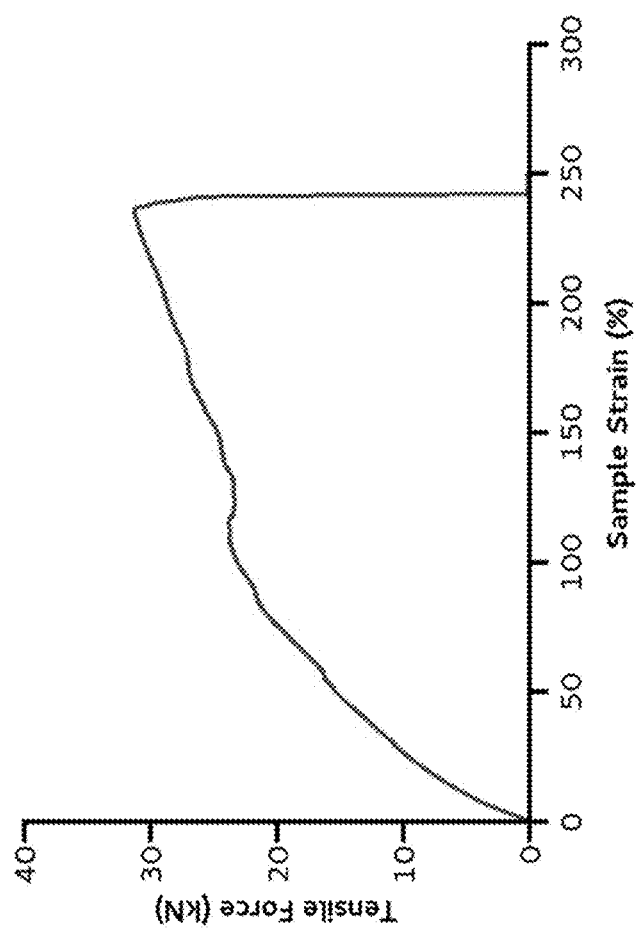
FIG. 6 shows a Stress-Strain curve obtained for the composite film, clearly depicting the fracture point at a strain of about 230%.

The stress-strain curve obtained on stretching the composite film is shown in FIG. 6. It can be seen that the film could be stretched to a strain of more than 225% before fracture. This demonstrates the synthesized composite film has a large stretchability. It can also be seen that the observed stress strain curve is similar to that of a thermoplastic polymer having a glass transition temperature below room temperature (Zhao et al. *ACS Applied Materials & Interfaces*, vol. 5, no. 18, pp. 9008-14, 2013). As PVA ideally behaves as such a thermoplastic polymer, it can be inferred that the mechanical properties of PVA dominates and the silver loading is small enough so as not to significantly affect the mechanical properties. This enables the composite to be able to stretch to such a large extent.

The sheet resistance measured using the four-point probe was approximately 85 $\Omega$/sq. Although there was some variation in the value when measured at different spots, this variance was small. Thus, it can be safely stated that the resistance in the film was uniform throughout. This could be achieved as the solution was thoroughly mixed during the synthesis process and the drop casted solution was uniformly cured in the drying oven at the appropriate temperature, leading to a very uniform film. The thickness of the film was about 350 microns. Multiplying the measured sheet resistance with the thickness of the film, the bulk resistivity of the film was calculated as about 3 $\Omega \cdot$cm. This value demonstrates that the synthesized composite material is highly conductive.

Figures 7A, 7B:
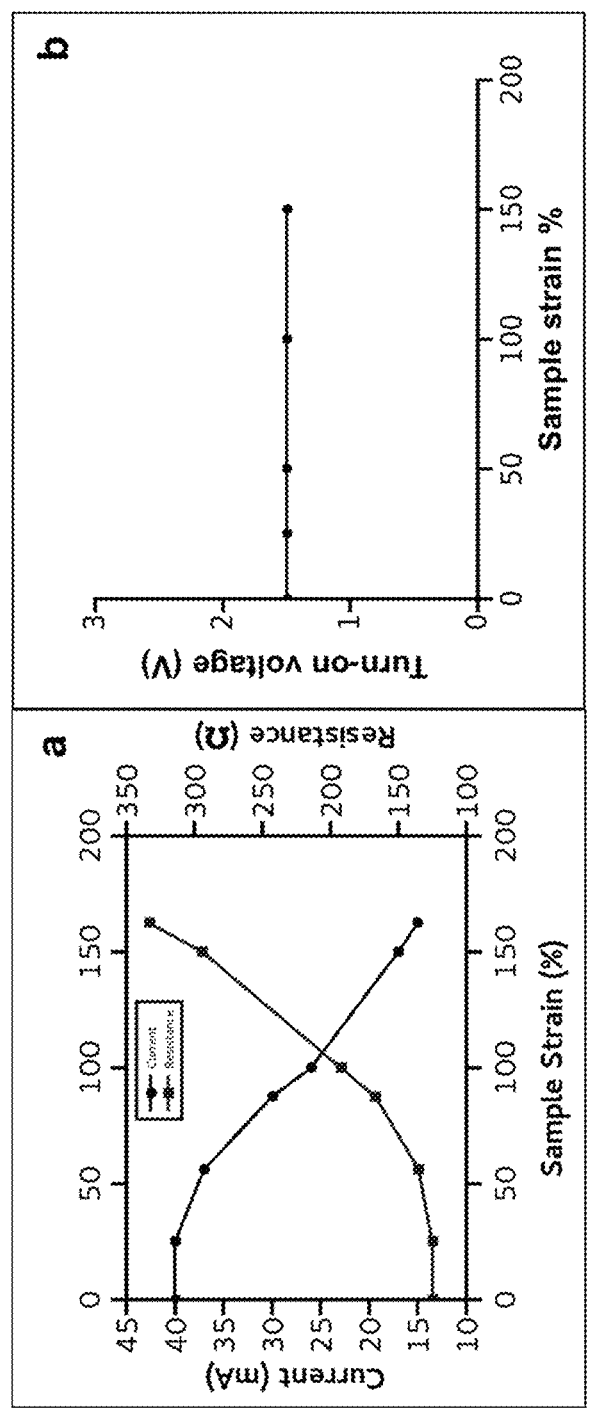
FIG. 7A shows a plot of measured current and calculated resistance for various percent strain of the film which had been subjected to fracture.
FIG. 7B shows the measured turn-on voltage of a red GaAs LED for various percent strain of the film which had been subjected to fracture.

FIG. 7A shows the current recorded flowing through the circuit set up to measure the resistance of the film for various percent strain of the film. As it can be safely assumed that the contact resistance is negligible as compared to the film resistance, the resistance of the film was calculated by dividing the applied voltage (about 5V) with the current observed. The observed current and the calculated resistance are shown as a function of the percent strain in FIG. 7A. FIG. 7B shows the voltage required to turn on the LED set up in the circuit shown in FIG. 2B at various percent strain of the film. It was observed that the turn on voltage for the GaAs LED did not change, even though the film is stretched as much as 150%. The turn on voltage stayed constant at about 1.5V for all percent elongation.

These experiments confirm the excellent electrical conductance of the polymer film. When the film is unstretched, the embedded silver flakes are packed closely enough to conduct electricity from one silver particle to another. And when the film is stretched, the PEDOT:PSS in the polymer backbone acts as a conductive pathway provider between adjacent silver particles to ensure that the flow of electricity is not hindered. Thus, the film exhibits high conductance even at high strains.

Thus, from the above results, it can be inferred that a highly stretchable and conductive composite material has been synthesized, which possesses high conductivity even at large strains. Without being limited to theory, this could be achieved because of the careful selection and optimization of the constituents used to synthesize the composite material and the careful optimization of the synthesis process. The high conductivity of the film can be attributed to efficient loading of the silver flakes along with assistance provided by the PEDOT:PSS in the polymer matrix. On the other hand, the large stretchability can be attributed to PVA and $H_3PO_4$. Inherently, pure PVA films can withstand large strains. However, the interaction of PVA with PEDOT:PSS would have decreased the ductility of the film owing to the brittle nature of PEDOT:PSS (Chen et al. *Synthetic Metals*, vol. 161, no. 21-22, pp. 2259-2267, 2011). $H_3PO_4$ may act as a plasticizer in the polymer matrix and help restore the large stretchability of the matrix (Zhao et al. *ACS Applied Materials & Interfaces*, vol. 5, no. 18, pp. 9008-14, 2013). Thus, the favorable interaction among all the constituent chemicals makes the high ductility and conductivity of the composite possible.

Figures 8A, 8B:
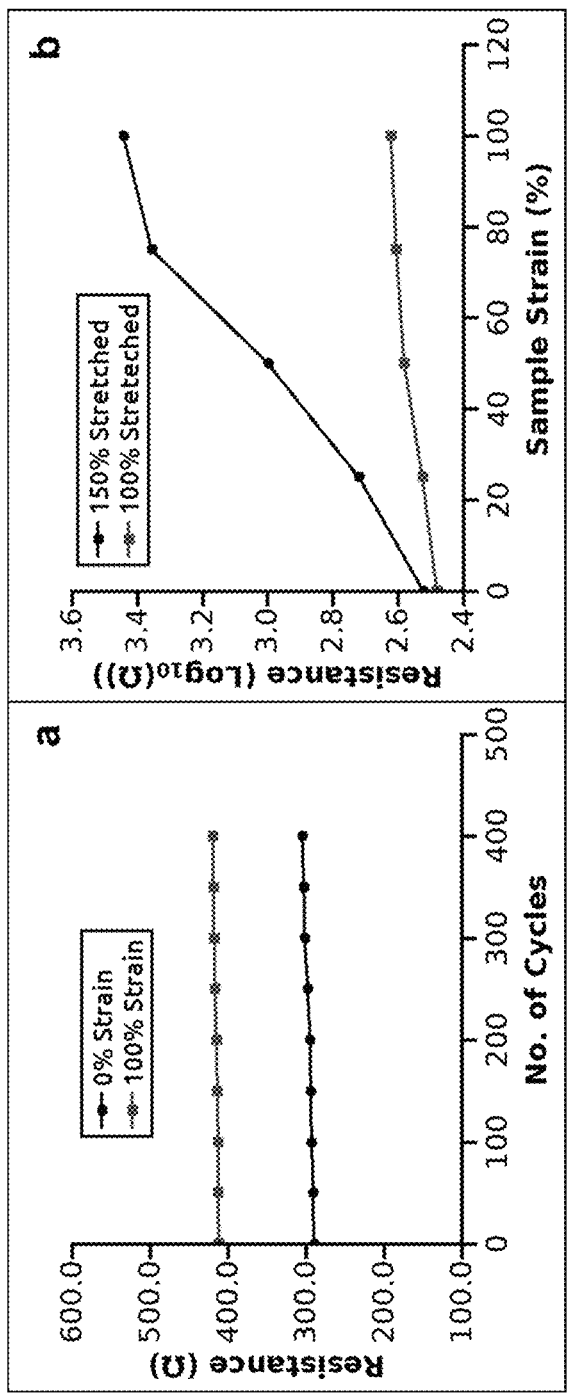
FIG. 8A shows in-situ resistance measurements of the composite film while being subjected to the fatigue test with maximum of about 100% strain.
FIG. 8B shows the calculated resistance for various percent strain of the films which had been subjected to fatigue cycles with maximum of about 100% strain and about 150% strain.

Electrical properties of composite films post fatigue cycling. FIG. 8A shows the in-situ resistance of the film that was stretched to about 100% and released continuously for 400 times. It can be seen that resistance of the film is low even after being stretched to 100%. It can also be seen that the resistance of the film does not change by any significant degree even after being subjected to 400 tension cycles. It was also observed that when the film was used a resistor to measure the turn-on voltage of the LED, the LED turned on at 1.5V even when the film was stretched to 100%. As mentioned in the section above, the silver content in the dominant phase was observed to have decreased after the 400 cycles. However, as the conductance of the film is maintained even after the fatigue test, it can be deduced that there were still sufficient silver particles in the polymer matrix and there still existed an electrical pathway between these particles to ensure good conductivity. Thus, even after 400 stretch cycles at 100%, the microstructure of the film does not get altered significantly to hamper the practical application of the film as a stretchable electronic material or as a stretchable interconnect.

FIG. 8B shows the resistance of the films as they are stretched to 100% after being subjected to the fatigue test. It can be seen that the resistance of the film which was stretched to about 150% and released continuously increased dramatically on being stretched above 25%. As was mentioned in the previous sections, the silver content in the dominant phase had decreased significantly after the 400 cycles. Thus, most likely, the microstructure of the film must have been altered notably such that the electrical pathway in the film got impeded at large strains. Thus, repeated strains at greater than about 150% could significantly reduce the useful life time of the film. However, it was also observed that when the film was used a resistor to measure the turn-on voltage of the LED, the LED still turned on at 1.5V even when the film was stretched to 100%. Thus, even after 400 cycles at such high strains, the composite film might still have some practical applications as a stretchable electronic material or as a stretchable interconnect.

Example 7

Strain Gauges

Construction of a Parallel Plate Capacitive Strain Gauge.

Figure 9A:
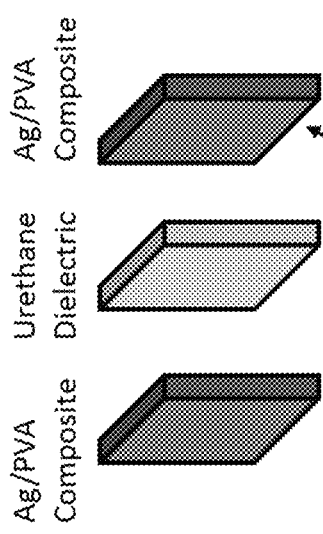
FIG. 9A shows a schematic of a urethane-based strain gauge and a picture of a stretchable silver polymer composite film.

A stretchable, flexible urethane rubber dielectric was made using Ure-Bond® (Smooth-on Inc.). The urethane was prepared using the provided instructions and materials without modification. To construct a parallel plate capacitive strain gauge, liquid urethane was dispensed onto the top surface of a pre-cut conductive polymer composite film sheet mounted to a glass microscope slide using double-sided tape. A second, pre-cut piece of conductive polymer composite film, also mounted to a glass slide, was then placed on top of the dispensed urethane, forming a sandwich structure as shown in FIG. 9A. The composite|urathane|composite sandwich was cured for about 24 hours at room temperature with a small weight placed over the sandwich to ensure good mechanical contact with the curing urethane. Enough urethane was applied such that the two conductive composites did not make contact with one another. After curing, the glass slides were removed and excess urethane cut away from the device area using a razor blade. The finished device was several centimeters long and about 1.25 cm wide with a urethane dielectric about 1 mm in thickness. The device was somewhat rigid when strained, due to its intended use as a high-force strain gauge.

Construction of an Interdigitated Capacitive Strain Gauge.

Figure 9B:
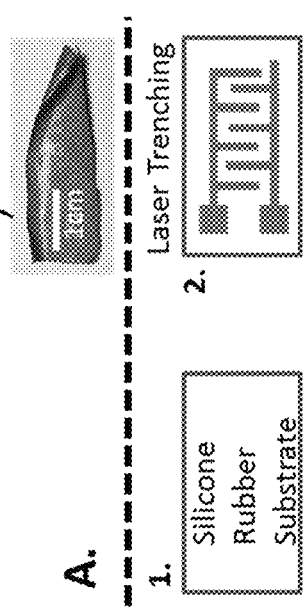
FIG. 9B shows a schematic illustrating the fabrication of an interdigitated strain gauge and a picture of a complete sensor after fabrication.
Figure 9B:
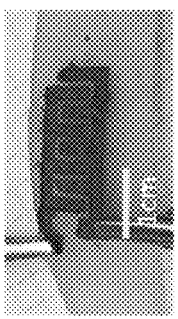

Stretchable, flexible, silicone rubber substrate was prepared using Ecoflex® 00-50 (Smooth-on Inc.). The silicone rubber was fabricated using the provided instructions without further modification. Viscous silicone rubber was poured into petri dishes and allowed to cure for about 5 hours, resulting in flat, uniform rubber sheets, about 3 mm in thickness. An interdigitated capacitor CAD design file was created using AutoCAD or Inkscape and carved into the silicone rubber substrate using an industrial laser cutter with a trench depth of about 1.5 mm. The liquid-phase Ag/PVA polymer composite blend was then dispensed into the trenches using a pipette and cured in a drying oven at about 70° C. for about 5 minutes. The complete sample device is shown in FIG. 9B.

Mathematical Modeling of an Interdigitated Strain Gauge.

Figure 10:
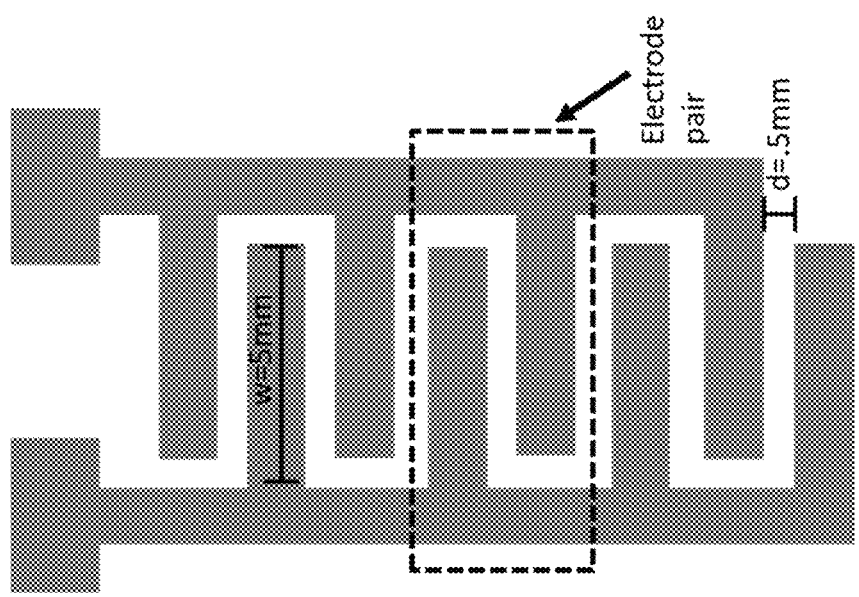
FIG. 10 shows geometrical parameters for a strain gauge simulation.

An interdigitated capacitor with three interlocking fingers was modeled at various strains using an Excel spreadsheet. The geometric dimensions chosen for the model were based on the measured dimensions of the fabricated strain gauge shown in FIG. 9B. The model assumed a dielectric constant of 4.2, in accordance with the Ecoflex® data sheet, and a Poisson's ratio of 0.5, which is the typical for silicone rubbers (J. A. Rinde, "Poisson's ratio for rigid plastic foams," *J Applied Polymer Science*, vol. 14, August 1970, pp. 1913-1926). The capacitance calculation was performed using the standard capacitance formula for an interdigitated capacitor:

$$C = \varepsilon_0 \varepsilon_r \frac{wt}{d} n$$

where $\varepsilon_r$ is the relative dielectric constant, d is the distance between the interdigitated electrode, w is the length of the electrode, t is the thickness of the electrode film, and n is the number of interdigitated electrode pairs. In this case, w is equal to 5 mm, t is equal to 1 mm, d is equal to 0.5 mm, and n is equal to 7 as shown in FIG. 10. As the device was strained, d became larger while t became smaller by a factor of 0.5 times strain percent.

Figure 11:
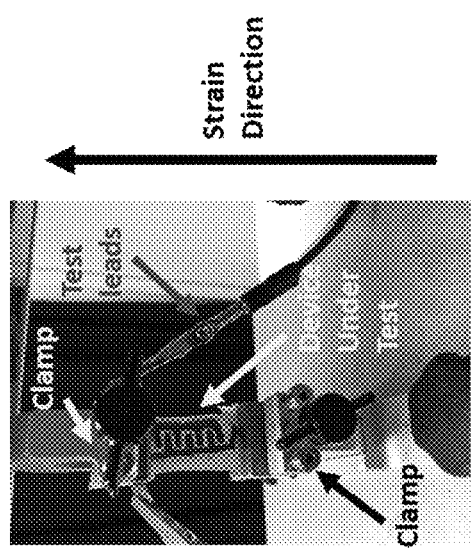
FIG. 11 shows a setup for tensile testing of an interdigitated strain gauge using a texture analyzer.

Capacitive strain gauges. Capacitive strain gauge devices were tested using a Ta.XT plus Texture Analyzer. Device samples were attached to the analyzer using a pair of sample clamps. The clamp pads were covered in scotch tape to ensure electrical isolation from any metal components. Pieces of copper foil, which were long enough to protrude away from the clamp-pad/device interface, were pinched between the tape-covered clamp pads and the device under test's two electrical contact points. The contact points were made of the silver/PVA composite and served as the capacitor terminals, as shown in FIG. 11. Care was taken to ensure good mechanical contact between the device contact points and the copper foil, and electrical connections were added to the original commercial instrument to monitor electrical properties while exerting a strain on the device under test.

Next, two pieces of copper foil were connected to a two-terminal capacitance meter using lead wires attached to alligator clips. The meter was pre-calibrated before being connected to the device terminals such that the capacitance of the meters' test leads could be negated from the device's capacitance measurement. The capacitance of the strain gauge under test was recorded as the texture analyzer applied a tensile strain force. In a typical experiment, a device was subjected to 50 strain cycles between two preset strain values: about 0% to about 36% for the urethane strain gauge, and about 0% to about 62% for the interdigitated strain gauge.

Results and Discussion.

Figures 12A, 12B:
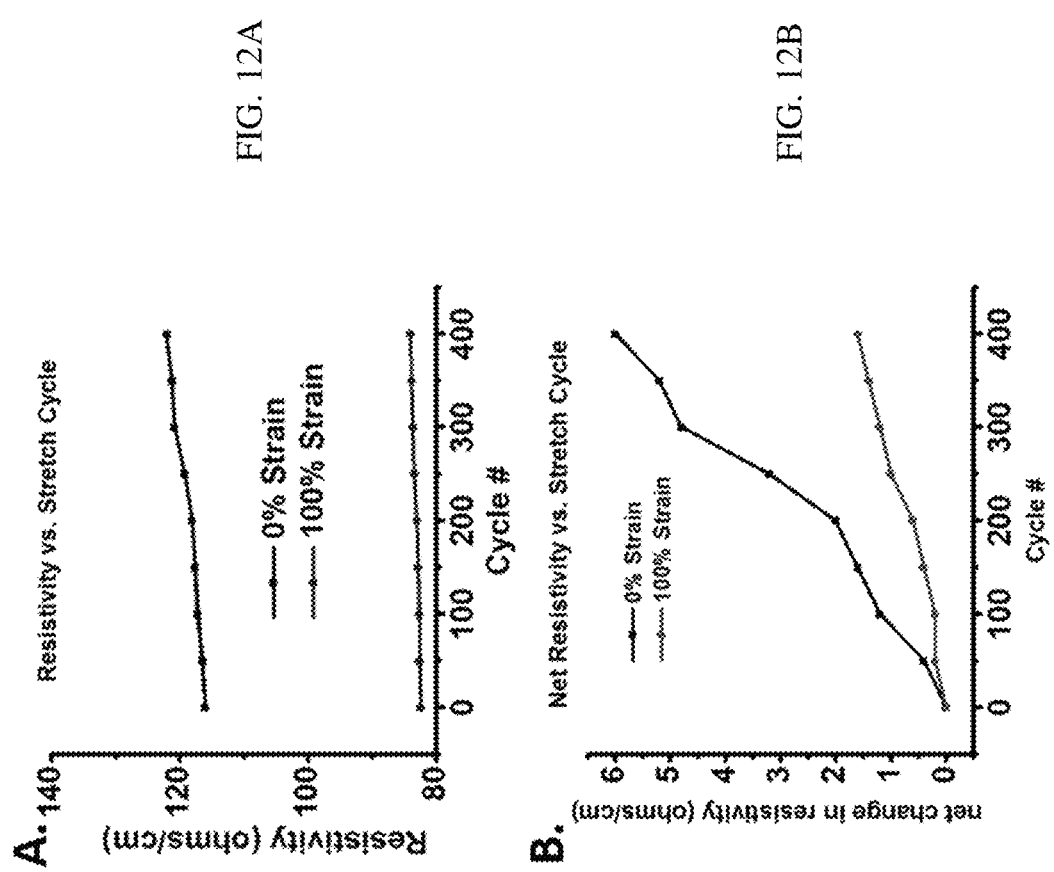
FIG. 12A shows a plot of resistivity vs. strain of a silver/PVA composite over 400 strain/relaxation cycles.
FIG. 12B shows a plot of net change in resistivity over 400 cycles.

Results of the in-situ fatigue test for the silver/PVA composite are shown in FIG. 12A. Intriguingly, the resistivity, ρ of the composite decreases with increasing strain. At 0% stain ρ is about equal to 117 Ω/cm before the strain cycle process begins. When the composite is stretched to 100% strain for the first time, ρ decreases to a value of about 81 Ω/cm, a decrease of about 30%. This result is somewhat counterintuitive; however, it can be explained using the resistivity equation for rectangular samples:

$$\rho = R(t*w)/L$$

where R is the measured resistance, t is the sample thickness, and L is the length. In the case of the silver/PVA composite sample, the value of L is increased by a factor of 2 during the strain test, while the value of R increases by a factor of 1.42, dividing 1.42/2 decreases ρ by 29%, which accounts for almost all the "lost" resistivity. The remaining 1% is likely due to decreasing values of w and t, but this analysis shows that the change in w and t does not significantly change the resistivity of the composite during stretching for the values of strain tested. This suggests that plotting the net change in resistivity vs. cycle count is more useful for obtaining fatigue information, as shown in FIG. 12B.

Over the course of 400 strain cycles, resistivity shows a small but noticeable increase of 6 Ω/cm and 1.6 Ω/cm at 0% and 100% strain, respectively. This suggests a high degree of mechanical reliability for the silver/PVA composite material.

Figures 13A, 13B:
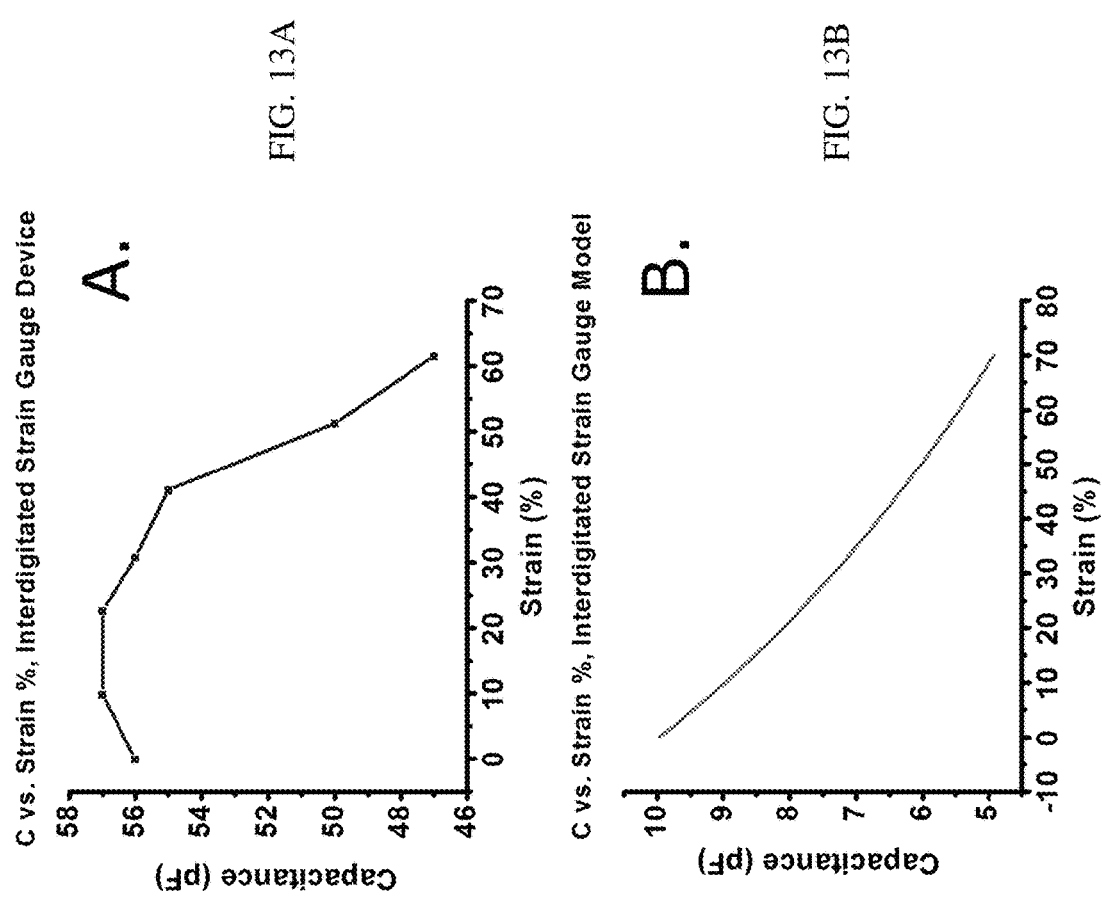
FIG. 13A shows a plot of an in-situ capacitance measurement of an interdigitated strain gauge subjected to tensile strain.
FIG. 13B shows a plot of capacitance change predicted from a three-finger model.

FIG. 13A shows the result of tensile testing test for the interdigitated capacitive strain sensor. The capacitance showed a general decreasing trend as the strain was increased. Capacitance of the device was equal to 56 pF at 0% strain. At 63% strain, the capacitance had dropped to 47 pF. This change is similar in magnitude to the values of capacitance predicted by the mathematical model of the device shown in FIG. 13B, using the physical parameters measured from the fabricated devices. This behavior is expected and has been well documented for previous interdigitated capacitive strain sensors (C. F. Hu., J. Y. Wang, Y. C. Liu, M. H. Tsai, W. Fang. *Nanotechnology*, vol. 24, 2013, pp. 1-14; R. Zeiser, T. Fellner, J. Wilde. *Journal of Sensors and Sensor Systems*, vol. 3, 2014, pp. 77-86; H. Cao, S. K. Thakar, M. L. Oseng, C. M. Nguyen, C. Jebali, A. B. Kouki, J. C. Chiao. *IEEE Sensors Journal*, vol. 15, 2015, pp. 6542-6548). The reason for the decrease is attributed to the fact that as the sensor is tensile strained, the distance between the adjacent digits increase. As capacitance is inversely related to the distance between the digits, the capacitance decreases. This holds true for the sensor when large strains were applied (>20%). However, it can be seen that for small strains, the capacitance did not vary much. It may be due to the opposite chemical natures of the silver polymer composite and the Ecoflex® substrate. The silver polymer composite is water-based while the substrate is hydrophobic in nature. Thus, the composite may not have adhered well to the surface of the substrate. Thus, at small strains, the composite may not have followed the strain being applied to the substrate, leading to no significant change in the capacitance. At larger strains, the composite may have gotten pressed against the grooves made in the substrate and was then able to follow the strain applied, which resulted in significant capacitance change. However, further experiments will be carried out with other substrate materials to verify that this was the cause of the low sensitivity in the low strain region. Despite this, the capacitive strain still shows high sensitivity for the larger strains, and the device could be used for certain strain sensing applications.

Figure 14:
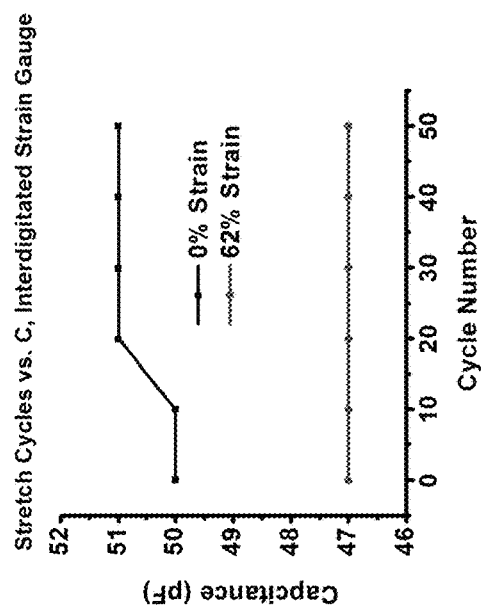
FIG. 14 shows an in-situ capacitance measurement of an interdigitated strain gauge subjected to fatigue testing with a device strain of about 62%.

FIG. 14 shows the in-situ capacitance of the sensor as it was stretched to 62% and released continuously for 50 times. As mentioned above, the capacitance in the strained state was noticeably lower than that in the unstrained state. It can also be seen that the capacitance values did not change by a significant degree even after 50 cycles. Thus, it can be inferred that the sensor is electromechanically durable to notable fatigue testing.

Figure 15:
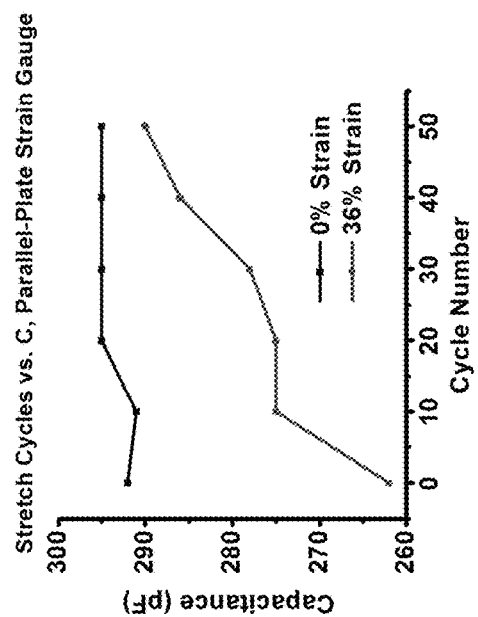
FIG. 15 shows an in-situ capacitance measurement of a urethane strain gauge subjected to fatigue testing under different strain conditions. Top curve: no strain applied while repeated capacitance measurements were performed. Bottom curve: device repeatedly strained to about 36% for 50 cycles.

FIG. 15 shows the in-situ capacitance of the urethane-based parallel plate capacitive sensor as it was stretched to 36% and released continuously for 50 times. Even for this sensor, the capacitance in the strained state was significantly lower than the unstrained state. It may be that as the capacitive sensor was very rigid, the applied strain caused shearing action on the plates, which in turn caused the cross-sectional area to decrease, resulting in a decrease in capacitance as the sensor was strained. It can also be observed that as the number of test cycles keep on increasing, the difference in capacitance between the strained and unstrained state kept on decreasing. This again can be attributed to the urethane being too rigid, most likely cracking down under repeated strains. It can be deduced from this that urethane may not be as good a material choice for the dielectric material for a parallel plate sensor. Further experiments will be carried out with other materials.

It is understood that the foregoing detailed description and accompanying examples are merely illustrative and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A composite comprising:
   a conductive polymer;
   a water-soluble polymer;
   a plasticizer; and
   metal flakes, wherein the metal flakes have a diameter of about 1 μm to about 45 μm, and
   wherein the plasticizer is phosphoric acid.

2. The composite of claim 1, wherein the conductive polymer is selected from the group consisting of poly(3,4-ethylenedioxythiophene)-poly(styrenesulfonate), polyacetylene, and polyphenylene vinylene.

3. The composite of claim 2, wherein the conductive polymer is poly(3,4-ethylenedioxythiophene)-poly(styrenesulfonate).

4. The composite of claim 3, wherein the poly(3,4-ethylenedioxythiophene)-poly(styrenesulfonate) includes poly(styrenesulfonate) and poly(3,4-ethylenedioxythiophene) in a weight ratio of about 1.0 to about 5.0.

5. The composite of claim 1, wherein the water-soluble polymer is selected from the group consisting of polyvinyl alcohol, polyethylene glycol, and polyvinylpyrrolidone.

6. The composite of claim 5, wherein the water-soluble polymer is polyvinyl alcohol.

7. The composite of claim 6, wherein the polyvinyl alcohol has a molecular weight of about 145 kDa to about 200 kDa.

8. The composite of claim 1, wherein the metal flakes comprise silver, copper, gold, platinum, zinc, or a mixture of any thereof.

9. The composite of claim 8, wherein the metal flakes are silver metal flakes.

10. A method of preparing a composite according to claim 1, comprising:
    dissolving the water-soluble polymer in water to form a first solution;
    adding the plasticizer to the first solution to form a second solution;
    adding a solution or suspension of the conductive polymer to the second solution to form a polymer blend; and
    adding the metal flakes to the polymer blend to form the composite.

11. The method of claim 10, further comprising drop casting and drying the composite.

12. A capacitive strain gauge comprising the composite according to claim 1.

13. The capacitive strain gauge according to claim 12, wherein the composite inhabits trenches in a silicone rubber substrate.

14. The capacitive strain gauge according to claim 13, wherein the substrate is about 3 mm thick and the trench is about 1.5 mm deep.

15. The capacitive strain gauge according to claim 12, wherein the gauge is an interdigitated capacitive strain gauge.

16. A method of preparing the capacitive strain gauge according to claim 12, comprising:
providing a sheet of silicone rubber;
laser cutting a trench into the silicone rubber sheet, wherein the trench is cut in an interdigitated configuration; and
dispensing the composite into the trench.

17. A method of preparing a composite, the method comprising:
providing a composite comprising
a conductive polymer;
a water-soluble polymer;
a plasticizer; and
metal flakes, wherein the metal flakes have a diameter of about 1 µm to about 45 µm dissolving the water-soluble polymer in water to form a first solution;
adding the plasticizer to the first solution to form a second solution;
adding a solution or suspension of the conductive polymer to the second solution to form a polymer blend; and
adding the metal flakes to the polymer blend to form the composite.

18. The method of claim 17, further comprising drop casting and drying the composite.

19. A capacitive strain gauge comprising:
a composite comprising
a conductive polymer;
a water-soluble polymer;
a plasticizer; and
metal flakes, wherein the metal flakes have a diameter of about 1 µm to about 45 µm wherein the composite inhabits trenches in a silicone rubber substrate.

20. The capacitive strain gauge according to claim 19, wherein the gauge is an interdigitated capacitive strain gauge.

* * * * *